United States Patent
Yoshimine

(10) Patent No.: US 10,231,748 B2
(45) Date of Patent: Mar. 19, 2019

(54) ULTRASONIC PROBE

(71) Applicant: OLYMPUS CORPORATION, Hachioji-shi, Tokyo (JP)

(72) Inventor: Hideto Yoshimine, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/482,031

(22) Filed: Apr. 7, 2017

(65) Prior Publication Data

US 2017/0209168 A1    Jul. 27, 2017

Related U.S. Application Data

(63) Continuation of application No. PCT/JP2015/076182, filed on Sep. 15, 2015.

(30) Foreign Application Priority Data

Jan. 7, 2015   (JP) .................................. 2015-001839

(51) Int. Cl.
*A61B 17/32* (2006.01)
*A61B 17/56* (2006.01)
(Continued)

(52) U.S. Cl.
CPC ...... *A61B 17/320068* (2013.01); *A61B 17/16* (2013.01); *A61B 17/1675* (2013.01);
(Continued)

(58) Field of Classification Search
CPC .............................................. A61B 17/320068
See application file for complete search history.

(56) References Cited

U.S. PATENT DOCUMENTS 5,318,570 A    6/1994   Hood et al.
5,318,579 A    6/1994   Chow
(Continued)

FOREIGN PATENT DOCUMENTS

JP    S60-236638 A    11/1985
JP    S62-211054 A    9/1987
(Continued)

OTHER PUBLICATIONS

Dec. 22, 2015 Search Report issued in International Application No. PCT/JP2015/076182.
(Continued)

*Primary Examiner* — Zade Coley
*Assistant Examiner* — Olivia C Chang
(74) *Attorney, Agent, or Firm* — Oliff PLC

(57) ABSTRACT

An ultrasonic probe includes a probe main body section to which the ultrasonic vibration is transmitted from its proximal end to its distal end; a curving section which is bent relative to the probe main body section; and a treating section which is continuous with a distal portion of the curving section to treat the knee joint. The curving section has a central axis which is bent at an angle of 5 degrees or more and 8 degrees or less relative to the longitudinal axis of the probe main body section, and is always disposed in a projection plane of the probe main body section, when the probe main body section is seen along a longitudinal axis from the proximal end toward the distal end.

12 Claims, 10 Drawing Sheets

(51) Int. Cl.
  *A61B 18/00* (2006.01)
  *A61B 17/16* (2006.01)
  *A61N 7/00* (2006.01)
  *A61B 17/00* (2006.01)
(52) U.S. Cl.
  CPC .............. *A61B 17/56* (2013.01); *A61B 18/00* (2013.01); *A61N 7/00* (2013.01); *A61B 2017/00402* (2013.01); *A61B 2017/00477* (2013.01); *A61B 2017/320072* (2013.01); *A61B 2018/00565* (2013.01); *A61B 2018/00922* (2013.01); *A61B 2018/00988* (2013.01); *A61B 2018/00994* (2013.01)

(56) References Cited

U.S. PATENT DOCUMENTS

| | | | | |
|---|---|---|---|---|
| 6,328,751 | B1 * | 12/2001 | Beaupre | A61B 17/320068 606/169 |
| 2009/0270891 | A1 | 10/2009 | Beaupre | |
| 2010/0057118 | A1 | 3/2010 | Dietz et al. | |

FOREIGN PATENT DOCUMENTS

| | | |
|---|---|---|
| JP | S62-213747 A | 9/1987 |
| JP | H04-212338 A | 8/1992 |
| JP | 2000-070279 A | 3/2000 |
| JP | 2005-152098 A | 6/2005 |
| JP | 2011-520544 A | 7/2011 |
| WO | 2010/047395 A1 | 4/2010 |

OTHER PUBLICATIONS

Oct. 4, 2016 Office Action issued in Japanese Patent Application No. 2016-550892.
Jul. 20, 2017 Notification and Translation of IPRP issued in International Application No. PCT/JP2015/076182.
Aug. 20, 2018 Search Report issued in European Patent Application No. 15876922.4.

* cited by examiner

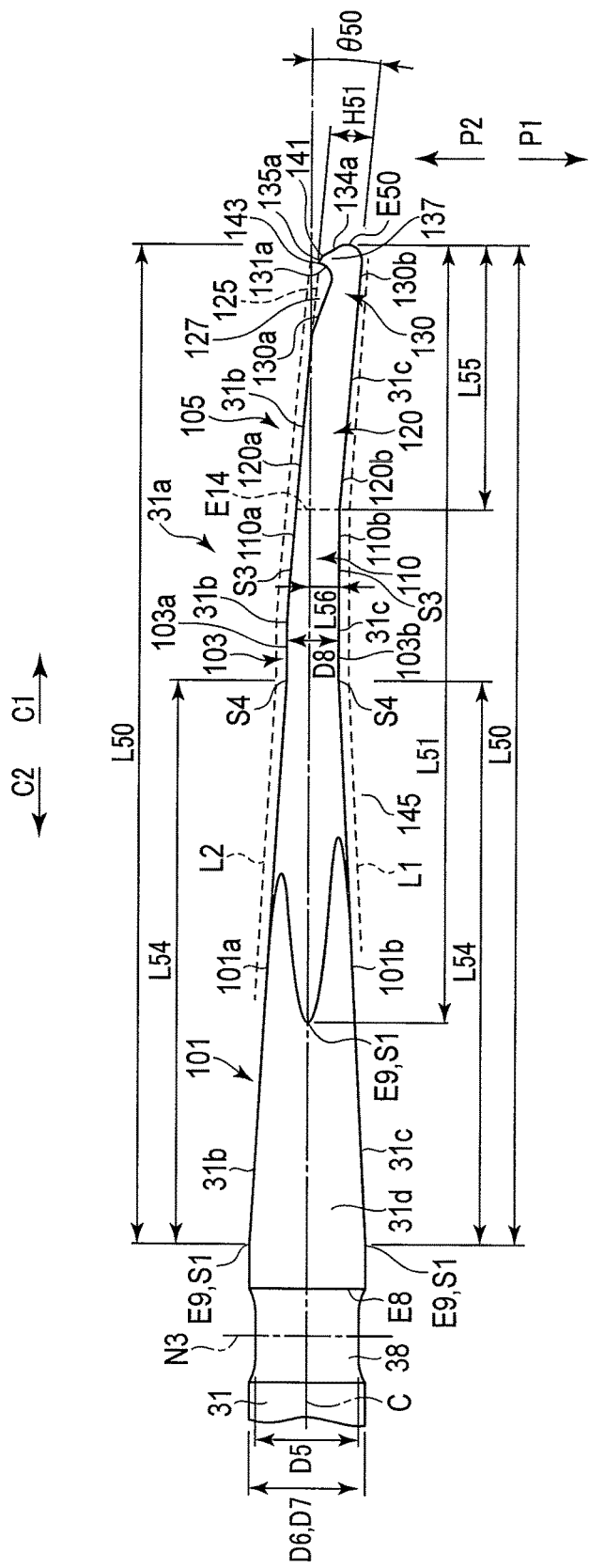
F I G. 3

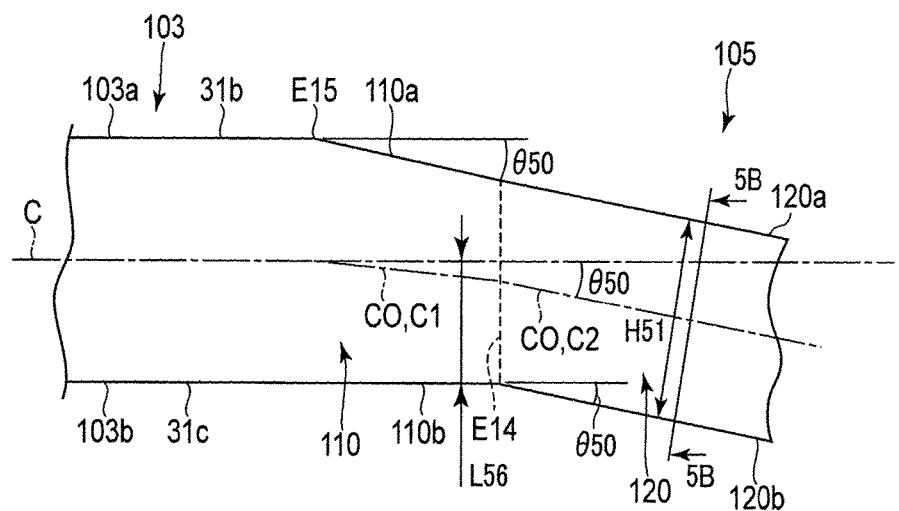
F I G. 5A
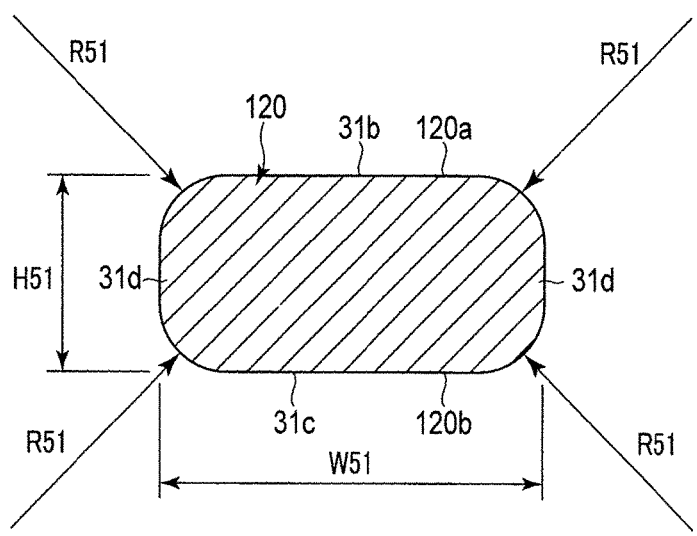
F I G. 5B

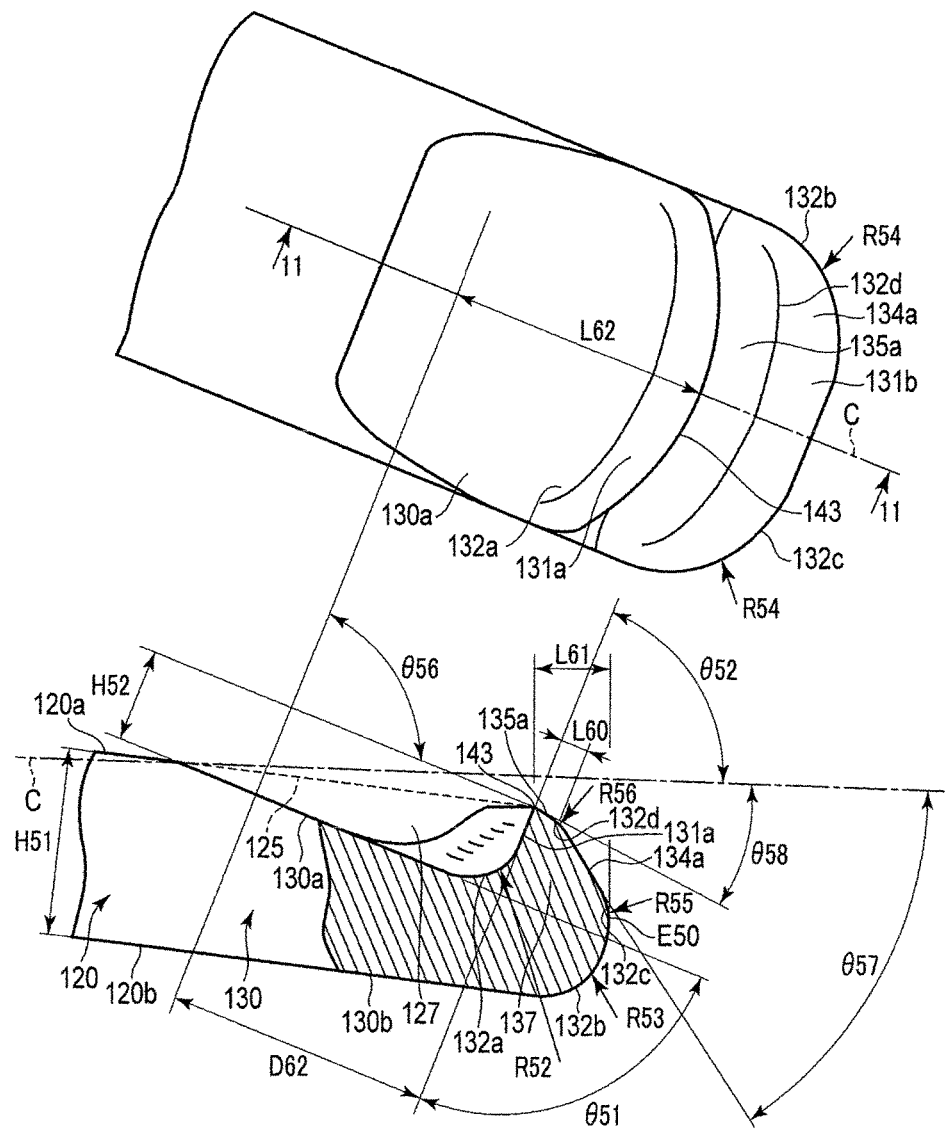
F I G. 11

ULTRASONIC PROBE

CROSS-REFERENCE TO RELATED APPLICATIONS

This application is a Continuation Application of PCT Application No. PCT/JP2015/076182, filed Sep. 15, 2015 and based upon and claiming the benefit of priority from prior Japanese Patent Application No. 2015-001839, filed Jan. 7, 2015, the entire contents of all of which are incorporated herein by reference.

BACKGROUND OF THE INVENTION

1. Field of the Invention

The present invention relates to an ultrasonic probe to perform cutting of, for example, a hard bone tissue and a cartilage tissue by ultrasonic vibration.

2. Description of the Related Art

In Jpn. Pat. Appln. KOKAI Publication No. 2005-152098, there is disclosed an ultrasonic treatment system including an ultrasonic probe (an ultrasonic horn). In this ultrasonic treatment system, an ultrasonic vibration generated in a vibration generating section (an ultrasonic vibration mechanism) is transmitted from a proximal toward a distal in the ultrasonic probe. In a distal portion of the ultrasonic probe, a scalpel portion is formed as a planar treating region.

In the scalpel portion, an outer surface of the ultrasonic probe is formed in an uneven state. The ultrasonic vibration is transmitted to the scalpel portion in a state where the scalpel portion is in contact with a treatment target, whereby an affected area is cut. The affected area is, for example, a bone or another hard tissue.

BRIEF SUMMARY OF THE INVENTION

According to an ultrasonic probe of one aspect of the invention, the ultrasonic probe for a knee joint to which ultrasonic vibration is transmitted to treat the knee joint by the ultrasonic vibration, includes a probe main body section which is extended along a longitudinal axis and to which the ultrasonic vibration is transmitted from its proximal end to its distal end; a curving section which is continuous with a distal portion of the probe main body section, and is bent relative to the probe main body section; and a treating section which is continuous with a distal portion of the curving section to treat the knee joint, wherein the curving section has a central axis which is bent at an angle of 5 degrees or more and 8 degrees or less relative to the longitudinal axis of the probe main body section, and is always disposed in a projection plane of the probe main body section, when the probe main body section is seen along the longitudinal axis from the proximal end toward the distal end.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a side view of a distal portion of a probe main body section according to the first embodiment;

FIG. 5A is an enlarged view around a sectional area decreasing portion shown in FIG. 3;

FIG. 5B is a cross-sectional view along the 5B-5B line shown in FIG. 5A;

FIG. 11 shows an enlarged view around a treating section shown in FIG. 10 and a cross-sectional view along the 11-11 line shown in FIG. 11.

DETAILED DESCRIPTION OF EMBODIMENTS

Hereinafter, embodiments of the present invention will be described in detail with reference to the drawings.

First Embodiment

A first embodiment will be described with reference to FIG. 1, FIG. 2, FIG. 3, FIG. 4, FIG. 5A, FIG. 5B, FIG. 6, FIG. 7, FIG. 8A and FIG. 8B. It is to be noted that in parts of drawings, diagrammatic representation of members of parts is omitted or simplified for clarification of the diagrammatic representation. In FIG. 3, a range shown with a broken line F1 and a broken line F2 projects to a distal side with respect to a distal end of a sheath 7.

Figure 1:
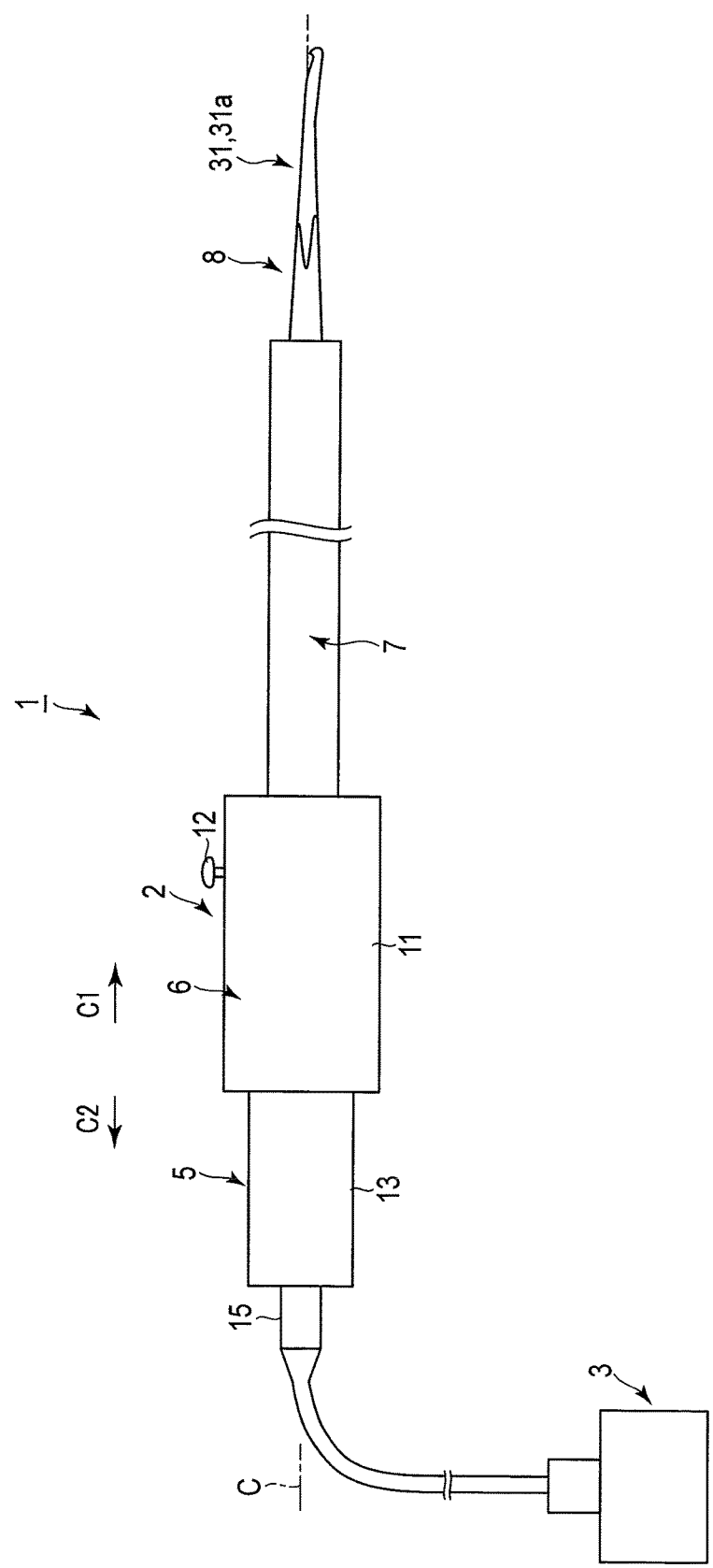
FIG. 1 is a view showing an ultrasonic treatment system according to a first embodiment of the present invention.

FIG. 1 is a view showing an ultrasonic treatment system 1 of the present embodiment. As shown in FIG. 1, the ultrasonic treatment system 1 includes an ultrasonic treatment instrument (a hand piece) 2, an energy control device 3, and a transducer unit 5. The ultrasonic treatment instrument 2 has a longitudinal axis C. Here, a direction parallel to the longitudinal axis C is a longitudinal axis direction. One side of the longitudinal axis direction is a distal side (an arrow C1 direction of FIG. 1), and a side opposite to the distal side is a proximal side (an arrow C2 direction of FIG. 1). The ultrasonic treatment instrument 2 of the present embodiment is, for example, for use in treating a knee joint by ultrasonic vibration.

The ultrasonic treatment instrument 2 includes a holding unit 6, the sheath 7, and an ultrasonic probe 8. The holding unit 6 includes a holding casing 11 to be held by an operator, and an energy operating button 12 that is an energy operation input section attached to the holding casing 11 and configured to be operated by the operator. The sheath 7 that is a hollow tubular member extending along the longitudinal axis C is coupled with the distal side of the holding unit 6. The ultrasonic probe (a vibration transmitting member) 8 is inserted through the sheath 7. It is to be noted that a distal portion of the ultrasonic probe 8 projects from a distal end of the sheath 7 toward the distal side. The ultrasonic probe 8 is, for example, an ultrasonic probe for the knee joint to which the ultrasonic vibration is transmitted to treat the knee joint by the ultrasonic vibration.

Furthermore, the transducer unit 5 having a transducer case 13 is coupled with the proximal side of the holding unit 6. The transducer unit 5 is connected to one end of a cable 15. The other end of the cable 15 is connected to the energy control device 3. The energy control device 3 is, for example, an energy treatment device. The energy control device 3 includes an electric power source, a conversion circuit to convert an electric power from the electric power source into a vibration generating electric power, a processor (a control section) including a CPU (central processing unit) or an ASIC (application specific integrated circuit), and a storage medium such as a memory. Inside the holding casing 11, there is disposed a switch (not shown) in which an ON/OFF state is changed by an input of an energy operation in the energy operating button 12. The switch is electrically connected to the processor of the energy control device 3 via a signal route extending through the transducer unit 5 and an inside of the cable 15. Furthermore, in the ultrasonic treatment system 1, a vibrating body unit 20 extends through an inside of the holding casing 11 and an inside of the transducer case 13.

Figure 2:
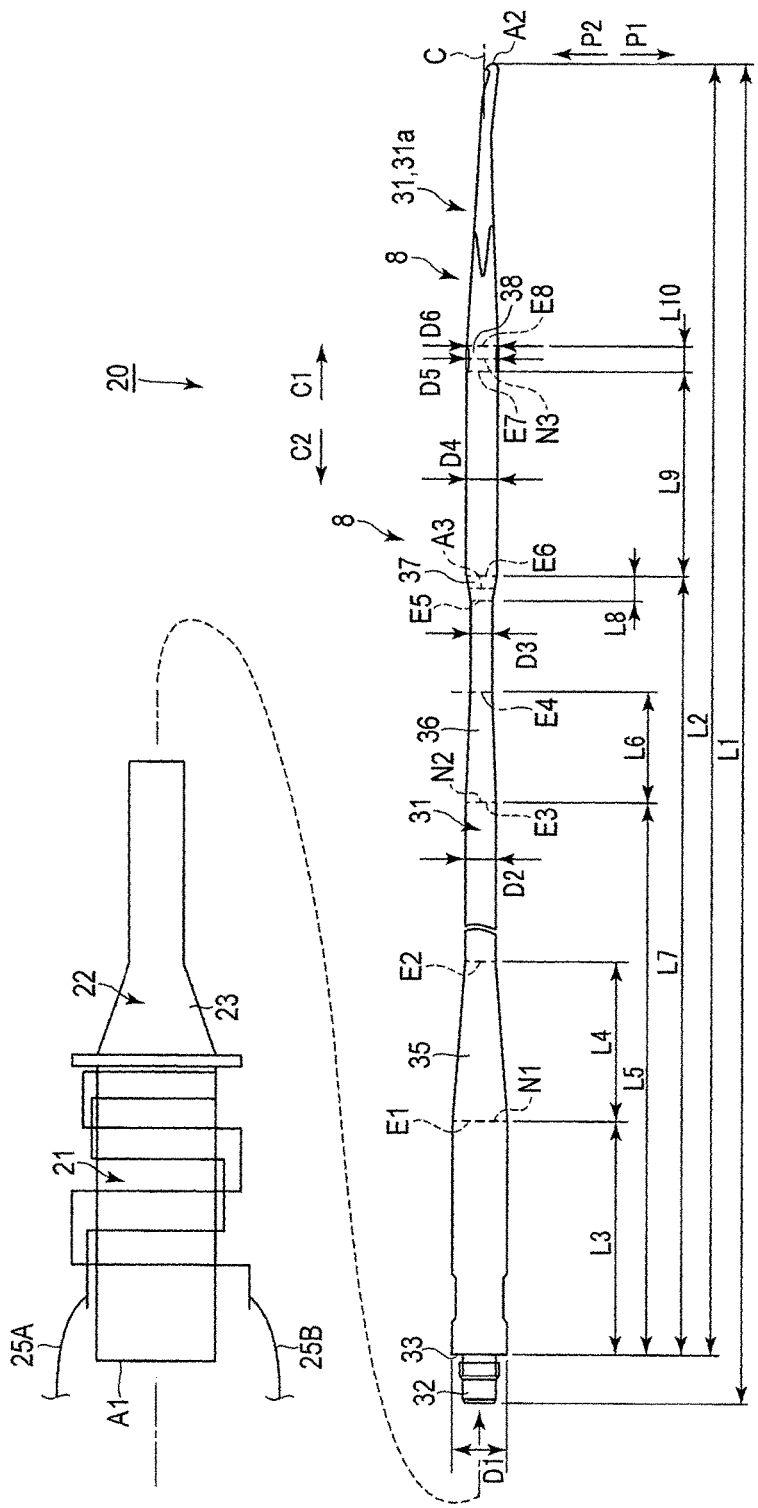
FIG. 2 is a view showing a constitution of a vibrating body unit.

FIG. 2 is a view showing a constitution of the vibrating body unit 20. As shown in FIG. 2, the vibrating body unit 20 includes the ultrasonic probe 8 mentioned above, an ultrasonic transducer 21 that is a vibration generating section constituted of piezoelectric elements, and a relay transmitting member 22. The ultrasonic transducer 21 and the relay transmitting member 22 are arranged in the transducer case 13, and the relay transmitting member 22 is supported by the transducer case 13. The ultrasonic transducer 21 is attached to the relay transmitting member 22. Inside the holding casing 11, the ultrasonic probe 8 is connected to the distal side of the relay transmitting member 22. In the relay transmitting member 22, a sectional area changing portion 23 is disposed in which a sectional area perpendicular to the longitudinal axis C decreases toward the distal side. The sectional area changing portion (a horn portion) 23 is positioned on the distal side with respect to the ultrasonic transducer 21. The ultrasonic transducer 21 is connected to one end of each of electric wires 25A and 25B. The electric wires 25A and 25B extend through the inside of the cable 15, and the other end of the wire is connected to the energy control device 3.

The switch is switched to an ON state by the input of the energy operation in the energy operating button 12, whereby in the energy control device 3, the control section controls the conversion circuit, to supply the vibration generating electric power (a vibration generating current) to the ultrasonic transducer 21 through the electric wires 25A and 25B. Consequently, in the ultrasonic transducer 21, the ultrasonic vibration occurs, and the generated ultrasonic vibration is transmitted to the ultrasonic probe 8 via the relay transmitting member 22. In this case, an amplitude of the ultrasonic vibration is enlarged in the sectional area changing portion 23 of the relay transmitting member 22.

[Probe Main Body Section 31]

The ultrasonic probe 8 includes a probe main body section 31 extending along the longitudinal axis C. The probe main body section 31 substantially linearly extends along the longitudinal axis C which is an axial center. On the proximal side of the probe main body section 31, an engagement connecting portion 32 is provided. The engagement connecting portion. 32 is engaged in an engagement groove (not shown) disposed in the relay transmitting member 22 (e.g., by screwing an external thread into an internal thread), whereby the probe main body section 31 is connected to the distal side of the relay transmitting member 22. Thus, the relay transmitting member 22 is connected to the probe main body section 31, whereby an abutment surface 33 formed at a proximal end of the probe main body section 31 abuts on the relay transmitting member 22. The ultrasonic vibration is transmitted from the relay transmitting member 22 to the probe main body section 31 through the abutment surface 33.

Thus, the ultrasonic vibration is transmitted to the probe main body section 31, whereby in the probe main body section 31 (the ultrasonic probe 8), the ultrasonic vibration is transmitted from the proximal toward the distal. In a state where the ultrasonic vibration is transmitted through the probe main body section 31, the vibrating body unit 20 performs a longitudinal vibration in a vibrating direction parallel to the longitudinal axis direction in a predetermined frequency range including a predetermined frequency. In this case, a vibration antinode (the most proximal vibration antinode) A1 that is one of vibration antinodes of the longitudinal vibration is positioned at a proximal end of the vibrating body unit 20 (a proximal end of the relay transmitting member 22), and a vibration antinode (the most distal vibration antinode) A2 that is one of the vibration antinodes of the longitudinal vibration is positioned at a distal end of the vibrating body unit 20 (a distal end of the ultrasonic probe 8). Here, the vibration antinode A1 is positioned most proximally among the vibration antinodes of the longitudinal vibration, and the vibration antinode A2 is positioned most proximally among the vibration antinodes of the longitudinal vibration. In a certain example, the vibrating body unit 20 is designed in a state of transmitting the ultrasonic vibration therethrough, thereby performing the longitudinal vibration at 47 kHz (the predetermined frequency), and the vibrating body unit actually longitudinally vibrates in the frequency range (the predetermined frequency range) of 46 kHz or more and 48 kHz or less.

The ultrasonic probe 8 has a total length L1 from its distal end to its proximal end (a proximal end of the engagement connecting portion 32) in the longitudinal axis direction. In the certain example, it is preferable that the total length L1 is 183.1 mm. Furthermore, the ultrasonic probe 8 has a longitudinal dimension L2 from the distal end to the abutment surface 33 (the proximal end of the probe main body section 31) in the longitudinal axis direction. In the certain example, it is preferable that the longitudinal dimension L2 is 177.1 mm.

In the probe main body section 31, a horn portion (a first horn portion) 35 is disposed. In the horn portion 35, the sectional area perpendicular to the longitudinal axis C decreases toward the distal side. The horn portion (a sectional area decreasing portion) 35 is positioned on the distal side with respect to the abutment surface 33, and the probe main body section 31 has a longitudinal dimension L3 from the abutment surface 33 to a proximal end (a vibration input end) E1 of the horn portion 35 in the longitudinal axis direction. In the certain example, it is preferable that the longitudinal dimension L3 is 29 mm. Furthermore, the horn portion (the first horn portion) 35 has a horn longitudinal dimension (a first horn longitudinal dimension) L4 from the proximal end (the vibration input end) E1 to a distal end (a vibration output end) E2 in the longitudinal axis direction. In the certain example, it is preferable that the horn longitudinal dimension L4 is 20 mm.

An outer diameter of the probe main body section 31 is kept to be substantially constant from the abutment surface 33 to the proximal end E1 of the horn portion 35 in the longitudinal axis direction. Therefore, the probe main body section 31 has an outer diameter D1 in the abutment surface 33 and at the proximal end E1 of the horn portion 35. In the certain example, it is preferable that the outer diameter D1 is 7 mm. Furthermore, in the horn portion 35, a sectional area decreases toward the distal side, and hence at the distal end E2 of the horn portion 35, the probe main body section 31 has an outer diameter D2 smaller than the outer diameter D1. That is, in the horn portion 35, the outer diameter of the probe main body section 31 decreases from the outer diameter D1 to the outer diameter D2 toward the distal side. In the certain example, it is preferable that the outer diameter D2 is 3.8 mm.

In a state where the vibrating body unit 20 longitudinally vibrates in the predetermined frequency range (e.g., 46 kHz or more and 48 kHz or less), a vibration node N1 that is one of vibration nodes of the longitudinal vibration is positioned at the proximal end E1 of the horn portion 35 or in the vicinity of the proximal end E1, and each of the vibration antinodes of the longitudinal vibration is positioned away from the horn portion 35 in the longitudinal axis direction. Consequently, in the horn portion 35 in which the sectional area decreases toward the distal side, the amplitude of the longitudinal vibration (the ultrasonic vibration) is enlarged. In the certain example, the longitudinal vibration in which the amplitude at the vibration antinode is 18 μm is transmitted to the proximal end E1 of the horn portion 35, and the amplitude of the longitudinal vibration in the horn portion 35 is enlarged. It is to be noted that in a state where the vibrating body unit 20 longitudinally vibrates at the predetermined frequency (e.g., 47 kHz) included in the predetermined frequency range, the vibration node N1 is positioned at the proximal end E1 of the horn portion 35.

In the probe main body section 31, a horn portion (a second horn portion) 36 is provided. In the horn portion 36, the sectional area perpendicular to the longitudinal axis C decreases toward the distal side. The horn portion (a sectional area decreasing portion) 36 is positioned on the distal side from the horn portion (the first horn portion) 35, and the probe main body section 31 has a longitudinal dimension L5 from the abutment surface 33 to a proximal end (a vibration input end) E3 of the horn portion 36 in the longitudinal axis direction. In the certain example, it is preferable that the longitudinal dimension L5 is 88.1 mm. Furthermore, the horn portion (the second horn portion) 36 has a horn longitudinal dimension (a second horn longitudinal dimension) L6 from the proximal end (the vibration input end) E3 to a distal end (a vibration output end) E4 in the longitudinal axis direction. In the certain example, it is preferable that the horn longitudinal dimension L6 is 14 mm.

In the probe main body section 31, the outer diameter is kept to be substantially constant from the distal end E2 of the horn portion (the first horn portion) 35 to the proximal end E3 of the horn portion (the second horn portion) 36 in the longitudinal axis direction. Therefore, the probe main body section 31 has the outer diameter D2 at the proximal end E3 of the horn portion 36. That is, at the distal end E2 of the horn portion 35 and the proximal end E3 of the horn portion 36, the outer diameter of the probe main body section 31 becomes the outer diameter D2 and has about the same size. Furthermore, in the horn portion 36, the sectional area decreases toward the distal side, and hence at the distal end E4 of the horn portion 36, the probe main body section 31 has an outer diameter D3 that is smaller than the outer diameter D2. That is, in the horn portion 36, the outer diameter of the probe main body section 31 decreases from the outer diameter D2 to the outer diameter D3 toward the distal side. In the certain example, it is preferable that the outer diameter D3 is 2.7 mm.

In the state where the vibrating body unit 20 longitudinally vibrates in the predetermined frequency range (e.g., 46 kHz or more and 48 kHz or less), a vibration node N2 that is one of the vibration nodes of the longitudinal vibration is positioned at the proximal end E3 of the horn portion 36 or in the vicinity of the proximal end E3, and each of the vibration antinodes of the longitudinal vibration is positioned away from the horn portion 36 in the longitudinal axis direction. Consequently, in the horn portion 36 in which the sectional area decreases toward the distal side, the amplitude of the longitudinal vibration (the ultrasonic vibration) is enlarged. It is to be noted that in the state where the vibrating body unit 20 longitudinally vibrates at the predetermined frequency (e.g., 47 kHz) included in the predetermined frequency range, the vibration node N2 is positioned at the proximal end E3 of the horn portion 36. Furthermore, in the state where the vibrating body unit 20 longitudinally vibrates in the predetermined frequency range, the vibration node N2 is positioned on the distal side with respect to the vibration node N1.

In the probe main body section 31, a sectional area increasing portion 37 is provided. In the sectional area increasing portion 37, the sectional area perpendicular to the longitudinal axis C increases toward the distal side. The sectional area increasing portion 37 is positioned on the distal side with respect to the horn portion (the second horn portion) 36, and the probe main body section 31 has a longitudinal dimension L7 from the abutment surface 33 to a distal end (a vibration output end) E6 of the sectional area increasing portion 37 in the longitudinal axis direction. In the certain example, it is preferable that the longitudinal dimension L7 is 116.7 mm. Furthermore, the sectional area increasing portion 37 has an extending dimension L8 from a proximal end (a vibration input end) E5 to the distal end (the vibration output end) E6 in the longitudinal axis direction. The extending dimension L8 is small, and hence in the sectional area increasing portion 37, a distance from the proximal end E5 to the distal end E6 decreases.

In the probe main body section 31, the outer diameter is kept to be substantially constant from the distal end E4 of the horn portion (the second horn portion) 36 to the proximal end E5 of the sectional area increasing portion 37 in the longitudinal axis direction. Therefore, the probe main body section 31 has the outer diameter D3 at the proximal end E5 of the sectional area increasing portion 37. That is, at the distal end E4 of the horn portion 36 and the proximal end E5 of the sectional area increasing portion 37, the outer diameter of the probe main body section 31 becomes the outer diameter D3 and has about the same size. Furthermore, in the sectional area increasing portion 37, the sectional area increases toward the distal side, and hence at the distal end E6 of the sectional area increasing portion 37, the probe main body section 31 has an outer diameter D4 that is larger than the outer diameter D3. That is, in the sectional area increasing portion 37, the outer diameter of the probe main body section 31 increases from the outer diameter D3 to the outer diameter D4 toward the distal side. In the certain example, the outer diameter D4 is about the same as the outer diameter D2 at the proximal end E3 of the horn portion 36. In this case, it is preferable that the outer diameter D4 is 3.8 mm.

In the state where the vibrating body unit 20 longitudinally vibrates in the predetermined frequency range, a vibration antinode A3 that is one of the vibration antinodes of the longitudinal vibration is positioned in the sectional area increasing portion 37. The vibration antinode A3 at which stress due to the ultrasonic vibration becomes zero is positioned in the sectional area increasing portion 37, and hence, also in the sectional area increasing portion 37 in which the sectional area increases toward the distal side, the amplitude of the longitudinal vibration (the ultrasonic vibration) hardly decreases. It is to be noted that in the state where the vibrating body unit 20 longitudinally vibrates in the predetermined frequency range, the vibration antinode A3 is positioned on the distal side with respect to the vibration node N2, and in the present embodiment, the vibration antinode A3 is positioned second distally among the vibration antinodes of the longitudinal vibration.

The probe main body section 31 includes a supported portion 38 by the sheath 7 via an elastic member (not shown). The supported portion 38 is positioned on the distal side with respect to the sectional area increasing portion 37. The probe main body section 31 has a longitudinal dimension L9 from the distal end E6 of the sectional area increasing portion 37 to a proximal end E7 of the supported portion 38 in the longitudinal axis direction. In the certain example, it is preferable that the longitudinal dimension L9 is 24.1 mm. Furthermore, the supported portion 38 has an extending dimension L10 from the proximal end E7 to a distal end E8 in the longitudinal axis direction. The extending dimension L10 is small, and in the certain example, it is preferable that the extending dimension L10 is 3 mm.

In the probe main body section 31, the outer diameter is kept to be substantially constant from the distal end E6 of the sectional area increasing portion 37 to the proximal end E7 of the supported portion 38 in the longitudinal axis direction. Therefore, the probe main body section 31 has the outer diameter D4 at the proximal end E7 of the supported portion 38. That is, at the distal end E6 of the sectional area increasing portion 37 and the proximal end E7 of the supported portion 38, the outer diameter of the probe main body section 31 becomes the outer diameter D4 and has about the same size. In a proximal portion of the supported portion 38, the outer diameter of the probe main body section 31 decreases from the outer diameter D4 to an outer diameter D5. In the certain example, the outer diameter D5 is about 0.4 mm smaller than the outer diameter D4. In the supported portion 38, the outer diameter of the probe main body section 31 is kept to be substantially constant at the outer diameter D5 along a large part in the longitudinal axis direction. Further, in the distal portion of the supported portion 38, the outer diameter of the probe main body section 31 increases from the outer diameter D5 to an outer diameter D6. In consequence, the probe main body section 31 has the outer diameter D6 at the distal end E8 of the supported portion 38. The outer diameter D6 at the distal end E8 of the supported portion 38 is about the same as the outer diameter D4 at the proximal end E7 of the supported portion 38. Consequently, at the proximal end E7 and the distal end E8 of the supported portion 38, the sectional area of the probe main body section 31 which is perpendicular to the longitudinal axis C becomes about the same. In the certain example, it is preferable that the outer diameter D6 is 3.8 mm.

In the state where the vibrating body unit 20 longitudinally vibrates in the predetermined frequency range, a vibration node N3 that is one of the vibration nodes of the longitudinal vibration is positioned in the supported portion 38. Consequently, the probe main body section 31 (the ultrasonic probe 8), which longitudinally vibrates, is also attached to the sheath 7 via the elastic member in the supported portion 38. Furthermore, the probe main body section is supported by the sheath 7 at the vibration node N3 of the longitudinal vibration, and hence in the state where the vibrating body unit 20 longitudinally vibrates in the predetermined frequency range, transmission of the ultrasonic vibration from the supported portion 38 to the sheath 7 is prevented. In the state where the vibrating body unit 20 longitudinally vibrates in the predetermined frequency range, the vibration node (the most distal vibration node) N3 is positioned on the distal side with respect to the vibration node N2, and is positioned most distally among the vibration nodes of the longitudinal vibration. Furthermore, at the proximal end E7 and the distal end E8 of the supported portion 38, the sectional area of the probe main body section 31 which is perpendicular to the longitudinal axis C becomes about the same, and hence in the supported portion 38, the amplitude of the longitudinal vibration hardly changes.

Furthermore, the distal end of the sheath 7 is positioned on the distal side with respect to the distal end E8 of the supported portion 38. Therefore, in the state where the vibrating body unit 20 longitudinally vibrates in the predetermined frequency range, the vibration node N3 positioned most distally among the vibration nodes is positioned inside the sheath 7. However, a distance between the distal end E8 of the supported portion 38 and the distal end of the sheath 7 in the longitudinal axis direction is small, and is about several mm in the certain example.

Figure 4:
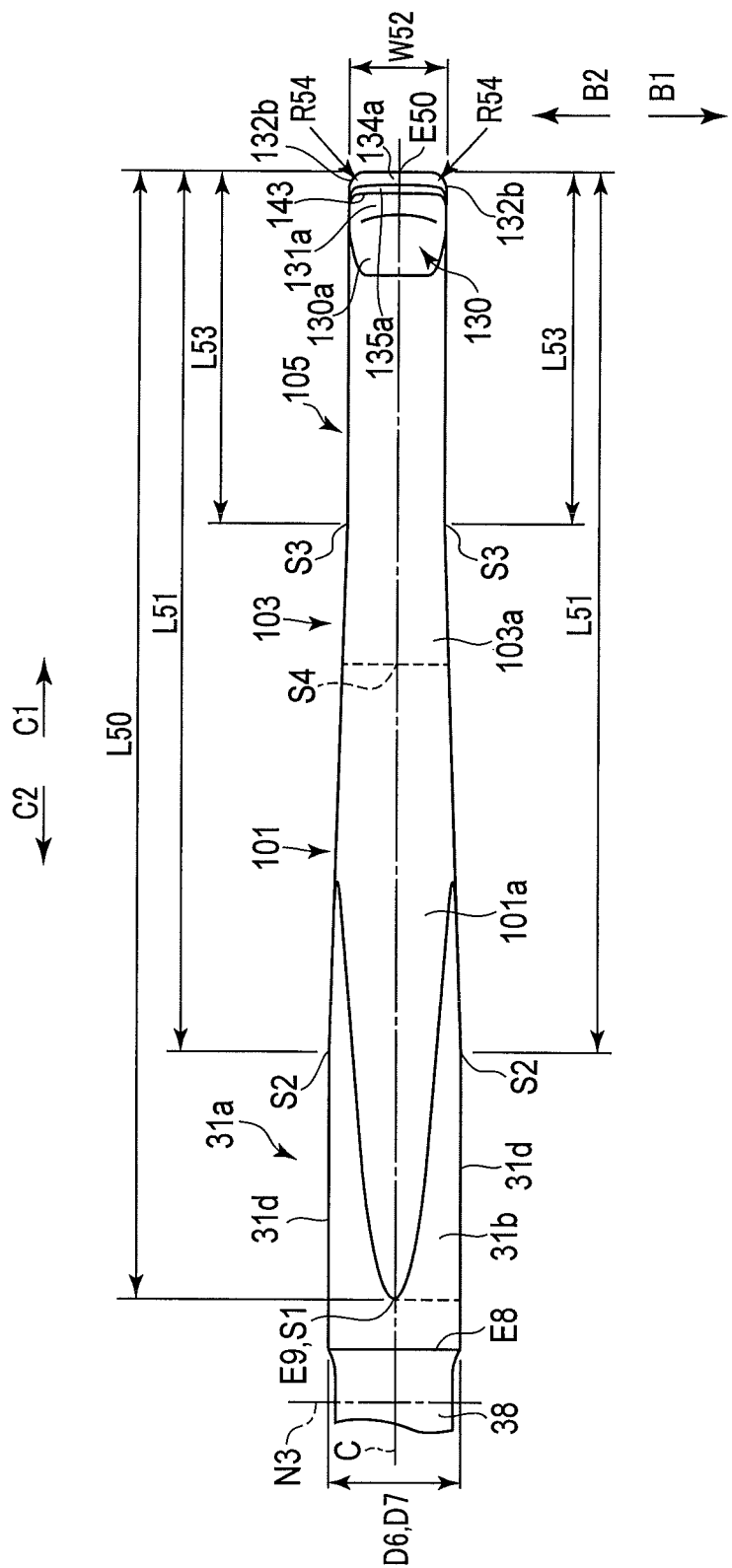
FIG. 4 is a top plan view of the distal portion of the probe main body section according to the first embodiment.

FIG. 3 and FIG. 4 are views showing a constitution of the distal portion of the ultrasonic probe 8. Here, a certain direction that is substantially perpendicular to (intersects) the longitudinal axis C is a first perpendicular direction (a direction of an arrow P1 in each of FIG. 2 and FIG. 3), and an opposite direction to the first perpendicular direction (a first intersecting direction) is a second perpendicular direction (a direction of an arrow P2 in each of FIG. 2 and FIG. 3). Furthermore, one of two directions which are substantially perpendicular to (intersect) the longitudinal axis C and are perpendicular to the first perpendicular direction (the first intersecting direction) and the second perpendicular direction (a second intersecting direction) is a first width direction (a direction of an arrow B1 in FIG. 4). Further, an opposite direction to the first width direction is a second width direction (a direction of an arrow B2 in FIG. 4). Here, FIG. 2 and FIG. 3 are views of the ultrasonic probe 8 seen from a first width direction side, and FIG. 4 is a view of the ultrasonic probe 8 seen from a second perpendicular direction side.

As shown in FIG. 3 and FIG. 4, the probe main body section 31 extends to a position located on the distal side with respect to the supported portion 38. That is, a distal end E9 of the probe main body section 31 is positioned on the distal side from the distal end E8 of the supported portion 38. However, a distance between the distal end E8 of the supported portion 38 and the distal end E9 of the probe main body section 31 in the longitudinal axis direction is small, and is about 0.6 mm in the certain example.

As described above, in the probe main body section 31, the amplitude of the longitudinal vibration is enlarged in the horn portion (the first horn portion) 35 and the horn portion (the second horn portion) 36, and the amplitude of the longitudinal vibration hardly changes in the sectional area increasing portion 37 and the supported portion 38. Due to the above-mentioned constitution, in the certain example, the longitudinal vibration of an amplitude of 80 μm occurs at the distal end E6 of the probe main body section 31, in a case where the longitudinal vibration of an amplitude of 18 μm at the vibration antinode is transmitted to the proximal end (the abutment surface 33) of the probe main body section 31.

[Distal Constituting Section 31a of Probe Main Body Section 31]

As shown in FIG. 1, the probe main body section 31 has a distal constituting section 31a which is exposed toward outside from the distal end of the sheath 7. For example, a part located on a forward side with respect to the distal end E8 of the supported portion 38 functions as the distal constituting section 31a.

As shown in FIG. 3, the distal constituting section 31a has a reference surface 31b including an after-mentioned blade tip portion 143, and an opposite surface 31c disposed on a side opposite to the reference surface 31b. The reference surface 31b is an upper surface of the probe main body section 31 and the opposite surface 31c is a lower surface of the probe main body section 31. The reference surface 31b and the opposite surface 31c are narrowed so that the probe main body section 31 tapers off toward a distal end E50 of the distal constituting section 31a. As shown in FIG. 3 and FIG. 4, on the reference surface 31b and the opposite surface 31c, a narrowing start position S1 is a position that is distant from the distal end E50 as much as a longitudinal dimension L50 in a longitudinal axis C direction. It is preferable that the longitudinal dimension L50 is 32 mm. The narrowing start position S1 is a continuous position of a proximal end of a tapered section 101 with the distal end E9 of the probe main body section 31, and is also a boundary position between the probe main body section 31 and the tapered section 101.

As shown in FIG. 3 and FIG. 4, in a circumferential direction of the probe main body section 31, the reference surface 31b and the opposite surface 31c are continuous with both side surfaces 31d of the probe main body section 31. As shown in FIG. 4, parts of the side surfaces 31d are narrowed to taper off toward the distal end E50. As shown in FIG. 3 and FIG. 4, on the side surfaces 31d, a narrowing start position S2 is a position that is distant as much as a longitudinal dimension L51 from the distal end E50 in the longitudinal axis C direction. It is preferable that the longitudinal dimension L51 is 25 mm. It is to be noted that a part of each side surface 31d is not narrowed, and as shown in FIG. 4, the narrowing end position S3 is a position that is distant as much as a longitudinal dimension L53 from the distal end E50. It is preferable that the longitudinal dimension L53 is 10 mm. Furthermore, between the narrowing start position S1 and the narrowing start position S2, the parts of the side surfaces 31d are not narrowed.

As shown in FIG. 3 and FIG. 4, the probe main body section 31 has the tapered section 101 (a sectional area decreasing portion), a relay extending section 103, and a curving section (a curved extending section) 105 which are provided in the distal constituting section 31a. A distal portion of the tapered section 101 is continuous with a proximal portion of the relay extending section 103, and a distal portion of the relay extending section 103 is continuous with a proximal portion of the curving section 105.

As shown in FIG. 3 and FIG. 4, it is preferable that a maximum outer diameter D7 of the tapered section 101 is 3.8 mm. It is preferable that a minimum outer diameter D8 of the tapered section 101 is 1.7 mm.

As shown in FIG. 3, a part 101a of the tapered section 101 is included in the reference surface 31b and is, for example, an upper surface of the tapered section 101. A part 101b of the tapered section 101 is included in the opposite surface 31c and is, for example, a lower surface of the tapered section 101. The parts 101a and 101b are narrowed from the narrowing start position S1 to the narrowing end position S4. The narrowing end position S4 is positioned forwardly from the narrowing start position S1. It is preferable that a longitudinal dimension L54 from the narrowing start position S1 to the narrowing end position S4 is 18 mm. The parts 101a and 101b function as an after-mentioned narrowing region.

As shown in FIG. 3 and FIG. 4, the side surfaces 31d of the distal portion in the tapered section 101 are narrowed from the narrowing start position S2 to the narrowing end position S4.

The side surfaces 31d in the proximal portion of the tapered section 101 are not narrowed, and this length is a length from the narrowing start position S1 to the narrowing start position S2.

In the tapered section 101, the sectional area perpendicular to the longitudinal axis C decreases toward the distal side. In the state where the vibrating body unit 20 longitudinally vibrates in the predetermined frequency range (e.g., 46 kHz or more and 48 kHz or less), the vibration node (the most distal vibration node) N3 that is one of the vibration nodes of the longitudinal vibration is positioned in the supported portion 38 and positioned in the vicinity of a proximal end (E9) of the tapered section 101. Further, in the state where the vibrating body unit 20 longitudinally vibrates in the predetermined frequency range, each of the vibration antinodes of the longitudinal vibration is positioned away from the tapered section 101 in the longitudinal axis direction. Consequently, in the tapered section 101 in which the sectional area decreases toward the distal side, the amplitude of the longitudinal vibration (the ultrasonic vibration) is enlarged. In the certain example, the distal end E50 longitudinally vibrates at 140 μm to 150 μm, in a case where the longitudinal vibration of an amplitude of 80 μm at the vibration antinode is transmitted to the proximal end (E9) of the tapered section 101.

Furthermore, in the present embodiment, a dimension of the tapered section 101 from the proximal end (E9) to a distal end (S4) in the longitudinal axis direction is larger than a ⅛ wavelength (λ/8) in the state where the vibrating body unit 20 longitudinally vibrates in the predetermined frequency range. In the certain example, in the state where the vibrating body unit 20 longitudinally vibrates at 46 kHz or more and 48 kHz or less (the predetermined frequency range), a ¼ wavelength (λ/4) from the vibration node (the most distal vibration node) N3 to the distal end E50 that is the vibration antinode (the most distal vibration antinode) A2 is 34.4 mm or more and 35.2 mm or less. On the other hand, in this example, a dimension from the proximal end (E9) of the tapered section 101 to the narrowing end position S3 in the longitudinal axis direction is about 22 mm, and is larger than the ⅛ wavelength in the state where the vibrating body unit 20 longitudinally vibrates at 46 kHz or more and 48 kHz or less (the predetermined frequency range). Furthermore, in the tapered section 101, it is preferable that the longitudinal dimension L54 between the proximal end (E9) and the narrowing end position S4 in the longitudinal axis direction is 17.9 mm or more and 18.1 mm or less. Therefore, the longitudinal dimension L54 is also larger than the ⅛ wavelength in the state where the vibrating body unit 20 longitudinally vibrates at 46 kHz or more and 48 kHz or less (the predetermined frequency range).

As shown in FIG. 3, the reference surface 31b and the opposite surface 31c in the relay extending section 103 are not narrowed but are arranged in parallel along the longitudinal axis C. As shown in FIG. 4, the side surfaces 31d in the distal portion of the relay extending section 103 are narrowed up from the narrowing end position S3 to the narrowing end position S4. A length of the relay extending section 103 is a length from the narrowing end position S3 to the narrowing end position S4. This region functions as an after-mentioned parallel region.

As shown in FIG. 5A, the curving section 105 has a central axis C0 that bends relative to the longitudinal axis C that is the central axis of the probe main body section 31. The central axis C0 of the curving section 105 bends away from the longitudinal axis C (toward the downside) from the proximal portion of the curving section 105 toward a distal portion of the curving section 105. The central axis C0 linearly extends. Further, as shown in FIG. 3 and FIG. 5A, the curving section 105 is bent relative to the probe main body section 31 on the distal side of the probe main body section 31. The curving section 105 linearly bends away from the longitudinal axis C. The bent curving section 105 is always disposed in a projection plane of the probe main body section 31, when the probe main body section 31 is seen along the longitudinal axis C from the proximal end toward the distal end. As shown in FIG. 4, in the curving section 105, the side surfaces 31d are not narrowed and the curving section corresponds to a portion having the longitudinal dimension L53.

Figure 6:
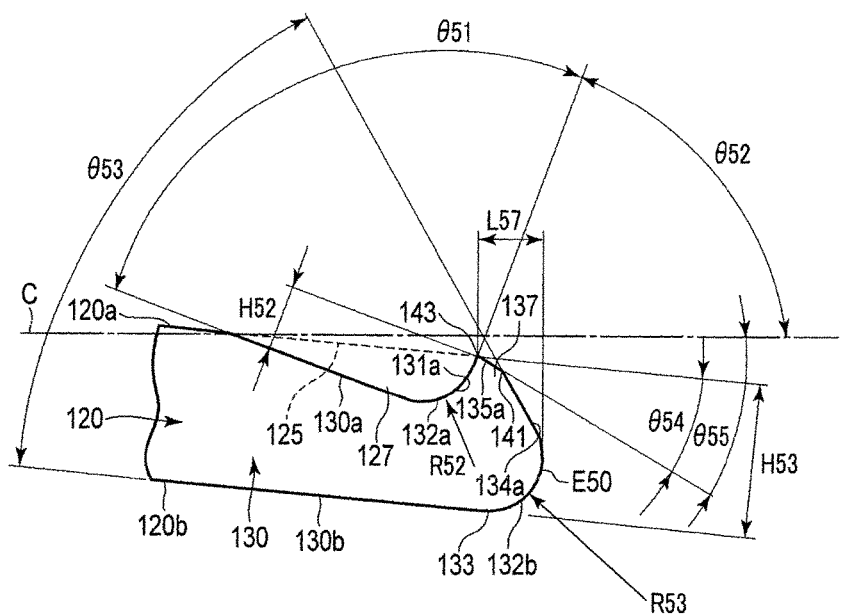
FIG. 6 is an enlarged view around a treating section shown in FIG. 3.

As shown in FIG. 3, FIG. 5A and FIG. 6, the curving section 105 has a sectional area decreasing portion 110, a sectional area uniform portion 120, and a treating section 130. A proximal portion of the sectional area decreasing portion 110 is continuous with the distal portion of the relay extending section 103. A proximal portion of the sectional area uniform portion 120 is continuous with a distal portion of the sectional area decreasing portion 110. A proximal portion of the treating section 130 is continuous with a distal portion of the sectional area uniform portion 120. The sectional area decreasing portion 110 is provided in the proximal portion of the curving section 105, the treating section 130 is continuous with the distal portion of the curving section 105, and the sectional area uniform portion 120 is interposed between the sectional area decreasing portion 110 and the treating section 130 and continuous with these portions. For example, a femur that is an affected area 200 in the knee joint is treated with the treating section 130.

As shown in FIG. 3 and FIG. 5A, a part 110a of the sectional area decreasing portion 110 is included in the reference surface 31b, and is, for example, an upper surface of the sectional area decreasing portion 110. The part 110a is narrowed into a tapered state. Specifically, the part 110a is linearly bent relative to the reference surface 31b in the relay extending section 103 in a direction to approach the longitudinal axis C (downwardly toward the longitudinal axis C). A bending angle θ50 is 5 degrees or more and 20 degrees or less.

As shown in FIG. 3 and FIG. 5A, a part 110b of the sectional area decreasing portion 110 is included in the opposite surface 31c and is, for example, a lower surface of the sectional area decreasing portion 110. The part 110b is disposed in parallel with the longitudinal axis C. It is preferable that a longitudinal dimension L56 between the part 110b and the longitudinal axis C is 0.95 mm.

As shown in FIG. 5A, due to the part 110a and the part 110b, the central axis C1 of the sectional area decreasing portion 110 which is included in the central axis C0 of the curving section 105 is linearly bent relative to the longitudinal axis C toward a direction away from the longitudinal axis C (downwardly from the longitudinal axis C).

As shown in FIG. 3 and FIG. 5A, the sectional area uniform portion 120 has a uniform thickness. As shown in FIG. 5A and FIG. 5B, it is preferable that a height H51 of the sectional area uniform portion 120 is 1.4 mm. It is preferable that a width W51 of the sectional area uniform portion 120 is 2.8 mm.

As shown in FIG. 5A, a part 120a of the sectional area uniform portion 120 is included in the reference surface 31b and is, for example, an upper surface of the sectional area uniform portion 120. The part 120a is continuous with the part 110a of the sectional area decreasing portion 110 included in the reference surface 31b, and is disposed on the same straight line as in the part 110a. Consequently, the part 120a is, similarly to the part 110a, linearly bent relative to the reference surface 31b in the relay extending section 103 toward a direction to approach the longitudinal axis C (downwardly toward the longitudinal axis C). A bending angle θ50 is 5 degrees or more and 20 degrees or less. As shown in FIG. 3 and FIG. 6, the part 120a extends up to the longitudinal axis C so that a distal portion of the part 120a intersects the longitudinal axis C.

As shown in FIG. 3 and FIG. 5A, the part 120a is continuous with the treating section 130, and functions as a first bending surface that bends relative to a peripheral surface of the probe main body section 31 to approach the longitudinal axis C, thereby intersecting the longitudinal axis C.

As shown in FIG. 3 and FIG. 5A, a part 120b of the sectional area uniform portion 120 is included in the opposite surface 31c, and is, for example, a lower surface of the sectional area uniform portion 120. The part 120a is continuous with the part 110b of the sectional area decreasing portion 110 included in the opposite surface 31c. The part 120b is linearly bent relative to the part 110b in the direction away from the longitudinal axis C (downwardly from the longitudinal axis C). A bending angle θ50 is 5 degrees or more and 20 degrees or less in the same manner as in the above-mentioned bending angles θ50. Consequently, the bending angles θ50 correspond to the bending angles of the part 110a and the circumferential surface of the sectional area uniform portion 120. In consequence, the part 120a is disposed in parallel with the part 120b. As shown in FIG. 3 and FIG. 6, a distal portion of the part 120b is positioned below the longitudinal axis C.

As shown in FIG. 5A, due to the part 120a and the part 120b, a central axis C2 of the sectional area uniform portion 120 which is included in the central axis C0 of the curving section 105 is linearly bent relative to the central axis C1 of the sectional area decreasing portion 110 toward the direction away from the longitudinal axis C (downwardly from the longitudinal axis C). A bending angle θ50 is 5 degrees or more and 20 degrees or less in the same manner as in the above-mentioned bending angles θ50. It is to be noted that the central axis C0 of the curving section 105 preferably bends at an angle of 5 degrees or more and 8 degrees or less relative to the longitudinal axis of the probe main body section 31. That is, it is preferable that the bending angle θ50 is 5 degrees or more and 8 degrees or less.

As shown in FIG. 3 and FIG. 5A, it is preferable that a longitudinal dimension L55 from the distal end E50 to a bending start position E14 of the opposite surface 31c is 8.5 mm. The bending start position E14 is a continuous region of the part 110b with the part 120b. Consequently, the curving section 105 is formed on the basis of the bending start position E14. The longitudinal dimension L55 indicates a sum of a length of the sectional area uniform portion 120 and a length of the treating section 130.

In the bending of the curving section 105, the curving section 105 includes an upper surface which includes a circumferential surface of the blade tip portion 143 and an after-mentioned projecting portion 137 that are a treating region and which is bent relative to an upper surface of the probe main body section 31, and a lower surface which is disposed on a side opposite to the upper surface of the curving section 105 with respect to the central axis C0 of the curving section 105, and which is bent relative to a lower surface of the probe main body section 31. The upper surface of the curving section 105 includes, for example, the part 110a, the part 120a, and a part 130a on the reference surface 31b. The lower surface of the curving section 105 includes, for example, the part 110b, the part 120b, and a part 130b on the opposite surface 31c. The upper surface of the probe main body section 31 is, for example, the part 103a of the relay extending section 103. The part 103a is included in the reference surface 31b, and is, for example, the upper surface of the relay extending section 103. The lower surface of the probe main body section 31 is, for example, a part 103b of the relay extending section 103 and part 110b. The part 103b is included in the opposite surface 31c in the same manner as in the part 110b. The part 103b is a lower surface of the relay extending section 103. A bending start position E15 of the upper surface of the curving section 105 relative to the upper surface of the probe main body section 31 is a continuous region of the part 103a with the part 110a. The bending start position E14 of the lower surface of the curving section 105 relative to the lower surface of the probe main body section 31 is a continuous region of the part 110b with the part 120b. The bending start position E15 is positioned on the proximal side with respect to the bending start position E14. The probe main body section 31 and the curving section 105 vibrate in the predetermined frequency range in a state where the ultrasonic vibration is transmitted from the probe main body section 31 to the curving section 105. In the state where the probe main body section 31 and the curving section 105 are vibrated in the predetermined frequency range, the bending start positions E14 and E15 are positioned forwardly, i.e., positioned on the distal side of the curving section 105 with respect to the most distal vibration node.

As shown in FIG. 4, it is preferable that a width W52 of the treating section 130 is 2.8 mm in the same manner as in the width W51 of the sectional area uniform portion 120.

As shown in FIG. 3 and FIG. 6, the part 130a of the treating section 130 is included in the reference surface 31b, and is, for example, an upper surface of the treating section 130. The part 130a is linearly bent relative to the part 120a of the sectional area uniform portion 120 included in the reference surface 31b, in the direction away from the longitudinal axis C (downwardly from the longitudinal axis C). The part 130a is disposed in the treating section 130, and functions as a second bending surface that bends relative to the first bending surface, in a bending direction of the part 120a as the first bending surface and a direction away from the longitudinal axis C.

As shown in FIG. 3 and FIG. 6, the part 130a smoothly curves into a circular shape, and is continuous with a part 131a included in the reference surface 31b. The part 131a is disposed in the treating section 130, and functions as a third bending surface that bends relative to the part 130a as the second bending surface in a direction to approach the longitudinal axis C on a side reverse to the bending direction of the part 120a as the first bending surface, and extends toward an extension line 125 of the part 120a as the first bending surface. The part 131a extends up to a position that is on the extension line 125 of the part 120a or a position below the extension line 125, toward the longitudinal axis C relative to the part 130a. The part 131a is, for example, the upper surface of the treating section 130.

As shown in FIG. 6, in a height direction of a curved surface portion 132a in the part 130a and the part 131a, a corner radius R52 is 0.5 mm. In the curved surface portion 132a, the part 131a tilts at an angle θ51 relative to the part 130a. The angle θ51 is 90 degrees. It is preferable that a height H52 of the part 131a relative to the part 130a is 0.6 mm. An angle θ52 formed between the longitudinal axis C direction and the part 131a is 55 degrees or more and 85 degrees or less.

As shown in FIG. 6, due to the parts 130a and 131a, a concave portion 127 is formed in a distal portion of the reference surface 31b.

As shown in FIG. 3 and FIG. 6, the part 130b of the treating section 130 is included in the opposite surface 31c, and is, for example, a lower surface of the treating section 130. The part 130b is continuous with the part 120b of the sectional area uniform portion 120 included in the opposite surface 31c, and is disposed on the same straight line as in the part 120b. The part 130b extends up to a region located forwardly from the curved surface portion 132a. The part 130b smoothly curves into a circular shape toward the longitudinal axis C and a rear side, and is continuous with a part 134a included in the reference surface 31b. The part 134a is, for example, the upper surface of the treating section 130.

As shown in FIG. 6, in a height direction of a curved surface portion 132b in the part 130b and the part 134a, a corner radius R53 is 0.5 mm. The part 134a tilts at an angle θ53 relative to the part 130b. The angle θ53 is 55 degrees. As shown in FIG. 4, in a width direction of the curved surface portion 132b, a corner radius R54 is 0.5 mm.

As shown in FIG. 6, a boundary point 133 between the part 130b and the curved surface portion 132b is a region which is most distant from the longitudinal axis C in the treating section 130, in a radius direction of the probe main body section 31. The boundary point 133 is positioned between the longitudinal axis C and the opposite surface 31c in one region (e.g., E9) of the tapered section 101 having the maximum outer diameter D7, in the radius direction of the probe main body section 31. That is, when the distal end is seen from the proximal end along the longitudinal axis C, the curving section 105 including the treating section 130 having the boundary point 133 is always disposed in the projection plane of the tapered section 101.

As shown in FIG. 3 and FIG. 6, the part 134a is bent rearward, and is continuous with a part 135a included in the reference surface 31b. This continuous region (a bent portion) functions as the blade tip portion 141. The blade tip portion 141 is linearly formed along the width directions (the arrow B2 direction) of the treating section 130, and is an end portion between the part 134a and the part 135a. The part 135a is, for example, the upper surface of the treating section 130.

As shown in FIG. 6, the part 135a is bent at an angle θ54 relative to the extension line 125. The angle θ54 is 25 degrees. In other words, the part 135a tilts at the angle θ54 relative to the central axis C2 of the sectional area uniform portion 120.

As shown in FIG. 3 and FIG. 6, the part 135a is continuous with the part 131a. The part 135a tilts at an angle θ55 around a continuous region between the part 135a and the part 131a toward the part 134a (away from the longitudinal axis C (downward)). The angle θ55 is 30 degrees or more and 45 degrees or less. The part 135a functions as a first treating surface that bends relative to the part 131a that is a third bending surface in the bending direction of the part 120a that is a first bending surface. It is to be noted that in the present embodiment, the part 134a is disposed forwardly with respect to the part 135a, and functions as a second treating surface that bends relative to the part 135a in the direction away from the longitudinal axis C.

As shown in FIG. 3 and FIG. 6, the continuous region between the part 135a and the part 131a functions as the blade tip portion 143. Consequently, the part 135a has the blade tip portion 143. Further, the part 135a bends relative to the blade tip portion 143 in the bending direction of the part 120a and a direction away from the extension line 125 of the part 120a, with the blade tip portion 143 being a center. Furthermore, the parts 134a and 135a tilt relative to the longitudinal axis C.

As shown in FIG. 6, it is preferable that a longitudinal dimension L57 in a longitudinal direction between the distal end E50 formed in the curved surface portion 132b and the blade tip portion 143 is 0.6 mm. As shown in FIG. 3, FIG. 4 and FIG. 6, the blade tip portion 143 is formed linearly along the width direction of the treating section 130, and is an end portion of the part 131a and the part 135a. It is preferable that a height H53 between the blade tip portion 143 and the boundary point 133 is 1.4 mm. The height H53 is a height of a distal portion of the treating section 130 including the projecting portion 137 that will be described later, and is shorter than the width W52 of the treating section 130. It is preferable that the width W52 is 2.8 mm as described above. A length of the part 135a (the first treating surface) along the longitudinal axis C is 25% or more of the longitudinal dimension L57 from the blade tip portion 143 (the treating region) to the distal end E20 of the curving section 105. The blade tip portion 143 is disposed at the highest position in the treating section 130, the part 131a and the part 135a. As shown in FIG. 6, the part 135a including the blade tip portion 143 is positioned on the extension line 125 of the part 120a or below the extension line 125. The blade tip portion 143 is disposed in a continuous region of the part 131a as the third bending surface with the part 135a as the first treating surface. As shown in FIG. 6, the blade tip portion 143 functions as a treating region positioned on the extension line 125 of the part 120a as the first bending surface or positioned on a side opposite to the longitudinal axis C with respect a boundary that is the extension line 125 of the part 120a as the first bending surface. That is, the blade tip portion 143 is disposed at a position that is on the extension line 125 or a position below the extension line 125.

As shown in FIG. 6, in the above-mentioned shape of the treating section 130, the treating section 130 has the projecting portion 137 projecting toward a side reverse to a bending direction of the central axis C0 of the curving section 105 relative to the longitudinal axis C, and the blade tip portion 143 of the treating region disposed at the end of the projecting portion 137 and therefore disposed at the position reverse to the bending direction of the central axis C0 relative to the longitudinal axis C to treat the knee joint.

The projecting portion 137 is, for example, a regional portion surrounded with the curved surface portion 132a and the parts 131a, 135a and 134a. The curved surface portion 132a and the parts 131a, 135a and 134a constitute a circumferential surface of the projecting portion 137. The end of the projecting portion 137 is a continuous region of the part 131a with the part 135a. A maximum height of the projecting portion 137 is the height H52 of the part 131a relative the part 130a.

In the distal constituting section 31a, the probe main body section 31 has the tapered section 101, the relay extending section 103 and the curving section (the curved extending section) 105 as described above. When a viewpoint is changed, the ultrasonic probe 8 has a narrowed region, a parallel region and an intersecting region.

As shown in FIG. 3, the narrowed region is disposed in the distal portion of the probe main body section 31 and is tapered and narrowed toward the longitudinal axis C. The narrowed region has the parts 101a and 101b. The parts 101a and 101b are vertically symmetrically arranged about the longitudinal axis C, and have the same length, shape and tilt as each other. Consequently, a narrowing angle on an upper surface is the same as a narrowing angle on a lower surface. The probe main body section 31 including the narrowed region and the curving section 105 vibrate in the predetermined frequency range in a state where the ultrasonic vibration is transmitted from the probe main body section 31 including the narrowed region to the curving section 105. In the state where the probe main body section 31 including the narrowed region and the curving section 105 are vibrated in the predetermined frequency range, the longitudinal dimension L54 is larger than a ⅛ wavelength of the vibration. The narrowed region and the treating section 130 disposed on the distal side with respect to the narrowed region are arranged in a ¼ wavelength of the vibration.

As shown in FIG. 3 and FIG. 5A, a parallel region is disposed forwardly with respect to the distal portion of the probe main body section 31 and the narrowed region, is continuous with the narrowed region, and is parallel to the longitudinal axis C. The parallel region has, for example, the reference surface 31b and the opposite surface 31c in the relay extending section 103, and the opposite surface 31c in the sectional area decreasing portion 110. In other words, the parallel region has, for example, the parts 103a and 103b of the relay extending section 103 and the part 110b of the sectional area decreasing portion 110. The reference surface 31b (the part 103a) is an upper surface that is parallel to the longitudinal axis C. The opposite surfaces 31c (the parts 103b and 110b) are lower surfaces which are arranged on a side opposite to the upper surface with respect to the longitudinal axis C, are parallel to the longitudinal axis C, and are longer than the upper surface. The part 103a and the part 103b are vertically symmetrically arranged about the longitudinal axis C, and have the same length and shape each other. The part 110b is provided, and hence the lower surface in the parallel region is longer than the upper surface in the parallel region, and extends to the distal side more than the upper surface in the parallel region.

As shown in FIG. 5A and FIG. 6, the intersecting region is disposed in the curving section 105, is continuous with the parallel region, and intersects the longitudinal axis C. The intersecting region has, for example, the reference surface 31b in the curving section 105. In other words, the intersecting region has the part 120a of the sectional area uniform portion 120.

As described above, the bent curving section 105 is always disposed in the projection plane of the probe main body section 31, when the probe main body section 31 is seen along the longitudinal axis C from its proximal end toward its distal end. Further, the part 101*b* is narrowed toward the longitudinal axis C. The continuous part 103*b* is continuous with the distal end of the part 101*b* and parallel to the longitudinal axis C, and the part 110*b* is continuous with the distal end of the part 103*b* and parallel to the longitudinal axis C. The parts 103*b* and 110*b* are always arranged in the projection plane of the probe main body section 31. The parts 120*b* and 130*b* are linearly bent in the direction away from the longitudinal axis C, but are always arranged in the projection plane of the probe main body section 31 in the same manner as in the parts 103*b* and 110*b*. Consequently, as shown in FIG. 3, a space 145 is formed on an opposite surface 31*c* side and in the projection plane of the probe main body section 31. The space 145 is positioned between the proximal end E9 (the proximal end of the part 101*a*) and the distal end of the part 130*b* in the longitudinal axis C direction, and positioned on the lateral side of the distal constituting section 31*a* of the probe main body section 31. The space 145 is disposed on a side reverse to the blade tip portion 143 with respect to the distal constituting section 31*a* of the probe main body section 31.

Operation and Advantageous Effects

Next, a function and an effect of the ultrasonic probe 8 of the present embodiment will be described.

For example, in a surgical operation under endoscope observation of, for example, the knee joint, an unshown port (opening) disposed to approach the affected area 200 is usually set at a predetermined position.

In the shape of the ultrasonic probe 8, when the ultrasonic probe 8 is seen from a proximal portion toward the distal portion of the ultrasonic probe 8 along the longitudinal axis of the ultrasonic probe 8, differently from the present embodiment, it is defined that the distal portion of the ultrasonic probe is bent relative to the proximal portion so that the distal portion of the ultrasonic probe 8 is always disposed outside the projection plane of the proximal portion of the ultrasonic probe. Further, it is defined that the treating section 130 is disposed in the distal portion. In this case, the port is usually narrow, a tubular member is thin, a cavity in the knee joint is narrow, and a circumferential surface of the femur is formed into a curved surface. Consequently, in the above-mentioned shape of the ultrasonic probe 8, inserting properties of the ultrasonic probe 8 to the tubular member and approaching properties of the treating region in the ultrasonic probe 8 to the affected area 200 would deteriorate. In the ultrasonic probe 8, a direction in which the affected area can be treated is determined in accordance with the vibrating direction. When the ultrasonic probe 8 does not come in contact with the affected area 200 in an appropriate state, an efficiency of the treatment deteriorates. Furthermore, the cavity is narrow, and the affected area is formed into the curved surface. Consequently, the above-mentioned shape of the ultrasonic probe 8 is not suitable to treat the affected area 200 in the narrow cavity. Furthermore, in the above-mentioned shape of the ultrasonic probe 8, the probe would come in contact with an area other than the affected area to damage the area other than the affected area, before coming in contact with the affected area. Consequently, the ultrasonic probe is not suitable to treat the affected area in the narrow cavity.

In the present embodiment, the curving section 105 is bent relative to the probe main body section 31. When a distal end of the curving section 105 is seen from its proximal end along the longitudinal axis C direction, the curving section 105 including the treating section 130 having the boundary point 133 is always disposed in the projection plane of the tapered section 101. The central axis of the curving section 105 bends at an angle of five degrees or more and eight degrees or less relative to the longitudinal axis C of the probe main body section 31.

Figure 8A:
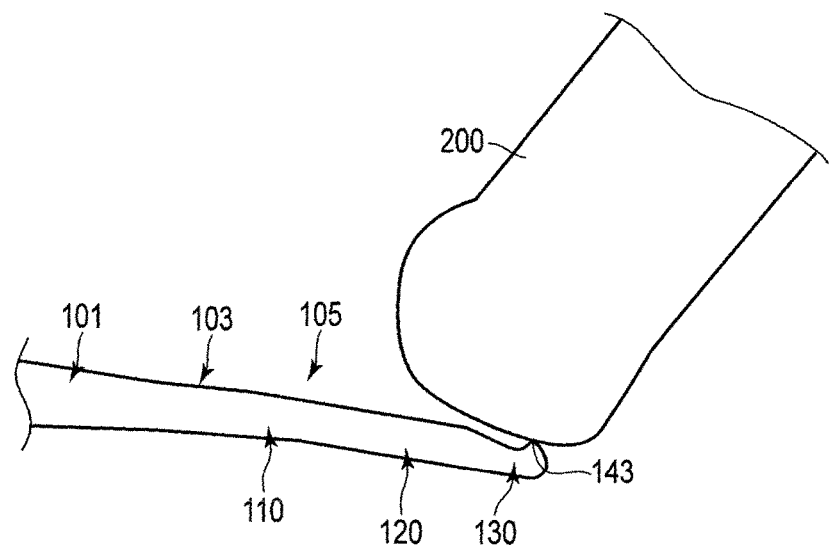
FIG. 8A is a view showing one example of a treatment of the ultrasonic probe.
Figure 8B:
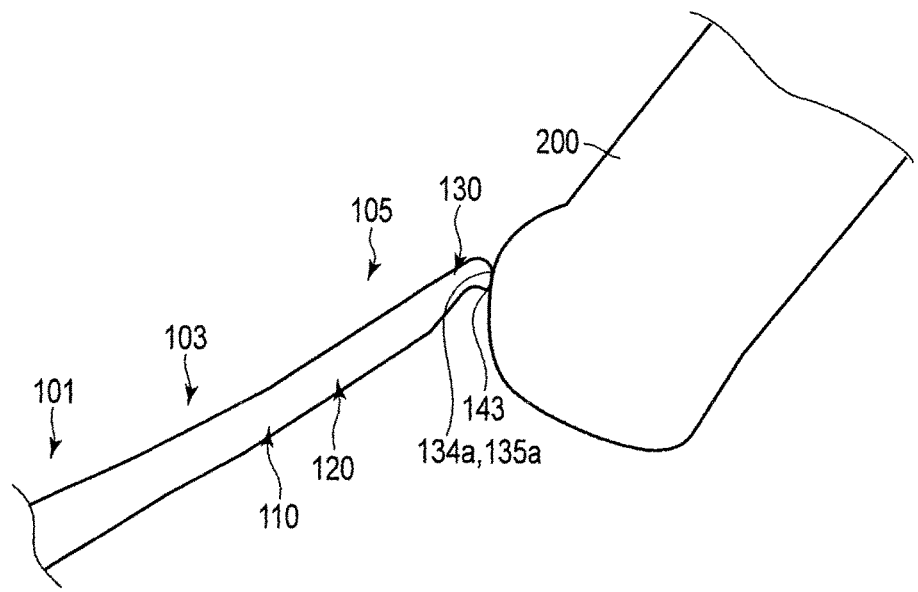
FIG. 8B is a view showing one example of a treatment of the ultrasonic probe.

Consequently, even when the port is narrow and the tubular member is thin, the inserting properties of the probe main body section 31 into the tubular member can improve in the probe main body section 31 having the curving section 105, as long as the probe main body section 31 is inserted into the tubular member. Furthermore, the probe main body section 31 having the curving section 105 can be inserted through the tubular member in accordance with a degree of the curve of the curving section 105, and during the insertion, the curving section 105 does not have to abut on an inner peripheral surface of the tubular member. Further, as shown in FIG. 8A and FIG. 8B, it is possible to improve the approaching properties of the blade tip portion 143 as the treating region in the ultrasonic probe 8 to the femur that is the affected area 200, and it is possible to improve the treatment efficiency to the affected area 200. In the present embodiment, as shown in FIG. 8A and FIG. 8B, by rotating the ultrasonic probe 8 around the axis of the probe main body section 31 and changing the orientation of the blade tip portion 143, it is possible to easily treat any regions of the femur and to improve the treatment efficiency and a treatment quality. In a case where the affected area 200 is present in the innermost area of the cruciate ligament, the blade tip portion 143 can easily approach the affected area 200.

In the present embodiment, the part 120*a* as the first bending surface is bent relative to the circumferential surface of the probe main body section 31 to approach the longitudinal axis C, thereby intersecting with the longitudinal axis C. Further, the blade tip portion 143 that is the treating region is positioned on the extension line 125 of the part 120*a* as the first bending surface. Alternatively, the extension line 125 of the part 120*a* that is the first bending surface is the boundary, and the blade tip portion is positioned on the side opposite to the longitudinal axis C with respect to the boundary. The blade tip portion 143 is linearly formed along the width direction of the treating section 130.

Consequently, even when a cavity between the femur and a tibia is narrow and a lower surface of the femur is formed into a curved surface, the affected area 200 can appropriately be treated with the ultrasonic probe 8 in accordance with the shape of the ultrasonic probe 8. Furthermore, the affected area is not limited to the knee joint, and in a narrow cavity of a joint (e.g., a shoulder joint) other than the knee joint, the affected area 200 can appropriately be treated with the ultrasonic probe 8 in accordance with the shape of the ultrasonic probe 8. Furthermore, as shown in FIG. 8A and FIG. 8B, it is possible to improve the approaching properties of the blade tip portion 143 as the treating region in the ultrasonic probe 8 to the femur that is the affected area 200, and it is possible to improve the treatment efficiency to the affected area 200. Especially, even when the probe main body section 31 is obliquely approached to the affected area 200, the blade tip portion 143 tilts, and hence the treatment efficiency can improve. Furthermore, in the present embodiment, as shown in FIG. 8A and FIG. 8B, by rotating the probe main body section 31 around the axis of the probe main body section 31 and changing an orientation of the blade tip portion 143, it is possible to easily treat any regions of the femur and to improve the treatment efficiency and the treatment quality. In the case where the affected area 200 is present in an innermost area of a cruciate ligament, the blade tip portion 143 can easily approach the affected area 200.

The blade tip portion 143 that is the treating region is disposed at a position on a side reverse to the bending direction of the central axis C0 of the curving section 105. Consequently, the blade tip portion 143 can always be disposed within a projection area of the probe main body section 31. When the probe main body section 31 is inserted into the thin tubular member, the blade tip portion 143 can be prevented from abutting on the inner peripheral surface of the tubular member. Furthermore, it is possible to improve the approaching properties of the blade tip portion 143 even to any regions of the femur.

The treating section 130 is a thin distal portion of the curving section 105. A height of the distal portion of the treating section 130 is shorter than a width of the treating section 130, and hence strength of the treating section 130 can be acquired in a state where the treating section 130 is thin. The strength is acquired, and hence even when an amplitude V of the longitudinal vibration is enlarged in the tapered section 101, the treating section 130 can be prevented from breaking. Furthermore, in the state where the breakage is prevented, the hard affected area 200, e.g., a bone or the like can be treated by use of the enlarged amplitude V of the longitudinal vibration. Furthermore, the treating section 130 is thin, and hence the treating section 130 can easily approach the affected area 200.

The bending start position E15 is positioned on the proximal side with respect to the bending start position E14. Consequently, the space 145 can be formed as an escaping portion, and hence the approaching properties to the affected area 200 can improve in the narrow cavity. Specifically, for example, the lower surface of the femur as the affected area 200 is treated. When the space 145 is formed, for example, the opposite surface 31c can be prevented from abutting on an upper surface of the tibia which faces the lower surface of the femur. That is, the area other than the affected area 200 can be prevented from being unintentionally treated, and prevented from being damaged. Further, the ultrasonic probe 8 can easily access the affected area 200 even in the narrow space. Furthermore, the distal portion of the curving section 105 can be thinned and lightened, and the treatment efficiency in the narrow cavity can improve.

The bending start positions E14 and E15 are positioned on a distal portion side of the curving section 105 with respect to the most distal vibration node N3. Consequently, the amplitude V of the longitudinal vibration which is enlarged in the tapered section 101 can be transmitted to the blade tip portion 143, and the treatment efficiency can improve.

The distal portion of the probe main body section 31 can be tapered by the narrowed region, the parallel region and the intersecting region, and the approaching properties can improve. Furthermore, the space 145 as the escaping portion can be formed, and hence the treatment efficiency in the narrow cavity can improve. Specifically, it is defined that, for example, the lower surface of the femur of the affected area 200 is treated. Thus, the space 145 is formed, so that, for example, the opposite surface 31c can be prevented from abutting on the upper surface of the tibia which faces the lower surface of the femur. That is, the area other than the affected area 200 can be prevented from being unintentionally treated, and can be prevented from being damaged. Further, the ultrasonic probe 8 can easily access the affected area 200 even in the narrow space. Furthermore, the distal portion of the curving section 105 can be thinned and lightened, and the treatment efficiency in the narrow cavity can improve.

In a case where the affected area 200 is hard as in, for example, the bone, it is necessary to enlarge the amplitude V of the longitudinal vibration. In the present embodiment, the amplitude V of the longitudinal vibration can securely be enlarged by the tapered section 101 including the narrowed region.

The part 135a including the blade tip portion 143 tilts at the angle θ55 relative to the longitudinal axis C toward the part 134a with the blade tip portion 143 being a center. Consequently, when the probe main body section 31 advances and retreats along the longitudinal axis C direction, for example, a side surface of the affected area 200 which is in the form of a curved surface can be treated by the part 135a including the blade tip portion 143.

The part 134a including the blade tip portions 141 and the part 135a including the blade tip portions 143 may cut the affected area 200. The affected area 200 is cut by the parts 134a and 135a, so that a region abraded by the blade tip portions 141 and 143 is prevented from being only concaved and a stepped area is prevented from being formed in the circumferential surface of the affected area 200.

The part 131a, the part 135a and the part 134a form the blade tip portions 141 and 143, i.e., blade tip portions are formed in two steps. Consequently, in the present embodiment, it is possible to acquire thickness and strength of the treating section 130 as compared with a case where only one blade tip portion located. Furthermore, a length of the first treating surface is 25% or more of the longitudinal dimension L57 from the blade tip portion 143 to the distal end of the curving section 105. Consequently, it is possible to acquire thickness and strength of the treating section 130. Thus, the strength is acquired, and hence even when the amplitude V of the longitudinal vibration is enlarged in the tapered section 101, it is possible to prevent breakage of the treating section 130. Further, in the state where the breakage is prevented, it is possible to treat the hard affected area 200, e.g., the bone or the like by use of the enlarged amplitude V of the longitudinal vibration.

In the present embodiment, the tapered section 101 and the relay extending section 103 are arranged, and a predetermined length is acquired. Consequently, even when the amplitude is enlarged, it is possible to prevent stress from being concentrated on a predetermined region of the distal constituting section 31a of the probe main body section 31, and it is possible to disperse the stress in the whole distal constituting section 31a of the probe main body section 31.

Figure 7:
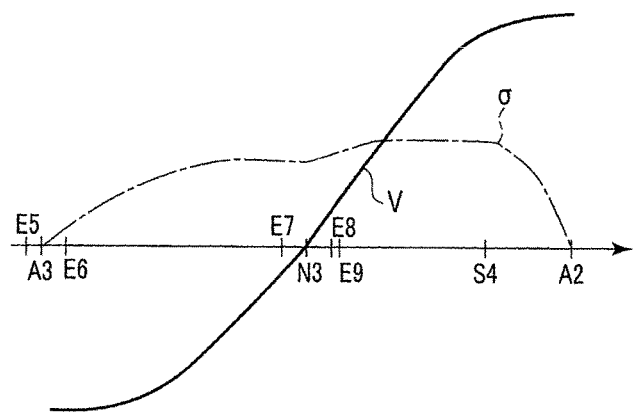
FIG. 7 is a schematic view showing an amplitude of a longitudinal vibration and stress due to an ultrasonic vibration between a second distal vibration antinode and a most distal vibration antinode in a state where the vibrating body unit according to the first embodiment longitudinally vibrates in a predetermined frequency range.

FIG. 7 shows the amplitude V of the longitudinal vibration and stress σ due to the ultrasonic vibration, between the second distal vibration antinode A3 and the most distal vibration antinode A2 in a state where the vibrating body unit 20 longitudinally vibrates in the predetermined frequency range. In FIG. 7, an abscissa shows a position in a longitudinal axis direction and an ordinate shows the amplitude V and the stress σ. Furthermore, in FIG. 7, a solid line shows change of the amplitude V of the longitudinal vibration and a one-dot chain line shows change of the stress σ.

As shown in FIG. 7, in a state where the vibrating body unit 20 longitudinally vibrates in the predetermined frequency range, the tapered section 101 is positioned on the distal side with respect to the most distal vibration node N3, and the amplitude V of the longitudinal vibration is enlarged in the tapered section 101. For example, the longitudinal vibration in which the amplitude at the vibration antinode is 80 μm is enlarged into the longitudinal vibration in which the amplitude at the vibration antinode is 140 μm or more and 150 μm or less by the tapered section 101. Furthermore, the stress σ due to the ultrasonic vibration increases at the vibration node and in a portion in which a sectional area perpendicular to a transmitting direction of the ultrasonic vibration decreases, and the stress becomes zero at the vibration antinode. Therefore, as shown in FIG. 7, the stress σ increases between the vibration node N3 and the narrowing end position S4 that is a distal end of the tapered section 101.

Here, in the present embodiment, a dimension from the proximal end (E9) of the tapered section 101 to the narrowing end position S4 in the longitudinal axis direction is larger than a ⅛ wavelength (λ/8) in the state where the vibrating body unit 20 longitudinally vibrates in the predetermined frequency range. Further, in the tapered section 101, the longitudinal dimension L54 between the proximal end (E9) and the narrowing end position S4 in the longitudinal axis direction is also larger than the ⅛ wavelength in the state where the vibrating body unit 20 longitudinally vibrates in the predetermined frequency range. The dimension from the proximal end (E9) of the tapered section 101 to the narrowing end position S4 in the longitudinal axis direction increases, so that the stress σ due to the ultrasonic vibration is kept to be substantially uniform along the total length between the vibration node N3 and the narrowing end position S4 of the tapered section 101. That is, between the vibration node N3 and the narrowing end position S4 of the tapered section 101, the stress is effectively prevented from locally increasing (i.e., generation of a peak is effectively prevented). For example, in a certain example, even when the longitudinal vibration (of, e.g., 80 μm) in which the amplitude at the vibration antinode increases is transmitted to the proximal end (E9) of the tapered section 101, the stress a is kept to be substantially uniform at about 300 Mpa between the vibration node N3 and the narrowing end position S4 of the tapered section 101 in the state where the vibrating body unit 20 longitudinally vibrates in the predetermined frequency range (e.g., 46 kHz or more and 48 kHz or less). That is, in the present embodiment, the stress is prevented from locally increasing up to about 700 Mpa between the vibration node N3 and the narrowing end position S4 of the tapered section 101 (e.g., at the narrowing end position S4 that is the distal end of the tapered section 101). The stress σ is prevented from locally increasing, and hence it is possible to effectively prevent the ultrasonic probe 8 from breaking due to the ultrasonic vibration.

In the present embodiment, in the case where the hard affected area 200, e.g., the bone or the like is treated with the ultrasonic probe 8 by use of the ultrasonic vibration, it is necessary to enlarge the amplitude V of the longitudinal vibration in the tapered section 101, and it is necessary to press the blade tip portion 143 onto the affected area 200. During the treatment, the tapered section 101 including the narrowed region and the curving section 105 would break due to the enlarged amplitude V and pressing. In the present embodiment, the longitudinal dimension L54 is larger than the ⅛ wavelength in the state where the vibrating body unit 20 of the ultrasonic probe 8 longitudinally vibrates. The narrowed region and the treating section 130 are arranged in a ¼ wavelength in the state where the vibrating body unit 20 longitudinally vibrates. Consequently, the stress is dispersed in the longitudinal dimension L54, that is, the stress is prevented from locally increasing as described above. Furthermore, the stress decreases in the relay extending section 103 and the curving section 105. Therefore, it is possible to effectively prevent the ultrasonic probe 8 from breaking due to the ultrasonic vibration, and the enlargement of the amplitude V is compatible with the prevention of the breakage.

In the present embodiment, the probe main body section 31 is formed so that any stepped areas are not formed, and the distal constituting section 31a of the probe main body section 31 is only narrowed.

Consequently, it is possible to inhibit generation of cavitation, and it is possible to prevent the cavitation from disturbing an observation view field when the affected area 200 is treated, in other words, an operator's visibility can improve. Further, it is possible to prevent the cavitation from damaging the affected area 200, and it is possible to prevent the cavitation from damaging the probe main body section 31 and the distal constituting section 31a. The corners R51 are formed in the periphery of the sectional area uniform portion 120, the corner R52 is formed in the curved surface portion 132a, and the corner R53 and the corner R54 are formed in the curved surface portion 132b of the part 130b. Consequently, in the sectional area uniform portion 120 and the curved surface portion 132b, it is possible to inhibit the generation of the cavitation and it is possible to prevent the cavitation from damaging the affected area 200.

Furthermore, in the above description, even when the sectional area uniform portion 120, the curved surface portion 132a and the curved surface portion 132b come in contact with the affected area 200, the corners R51, R52, R53 and R54 can prevent damages on the affected area 200. A curved surface portion of the corner radius R51 may be formed along ranges F1 and F2 of FIG. 3 in the longitudinal axis direction. That is, the curved surface portion of the corner radius R51 extends from the distal end of the ultrasonic probe 8 to the tapered section 101 in the longitudinal axis direction, and is formed in a projecting portion (an exposed portion) of the ultrasonic probe 8 from the distal end of the sheath 7.

Second Embodiment

In the present embodiment, differences from the first embodiment will only be described with reference to FIG. 9, FIG. 10 and FIG. 11.

It is preferable that a total length L1 is 183.2 mm. It is preferable that a longitudinal dimension L2 is 177.2 mm. A longitudinal dimension L53 is preferably 10 mm.

Figure 9:
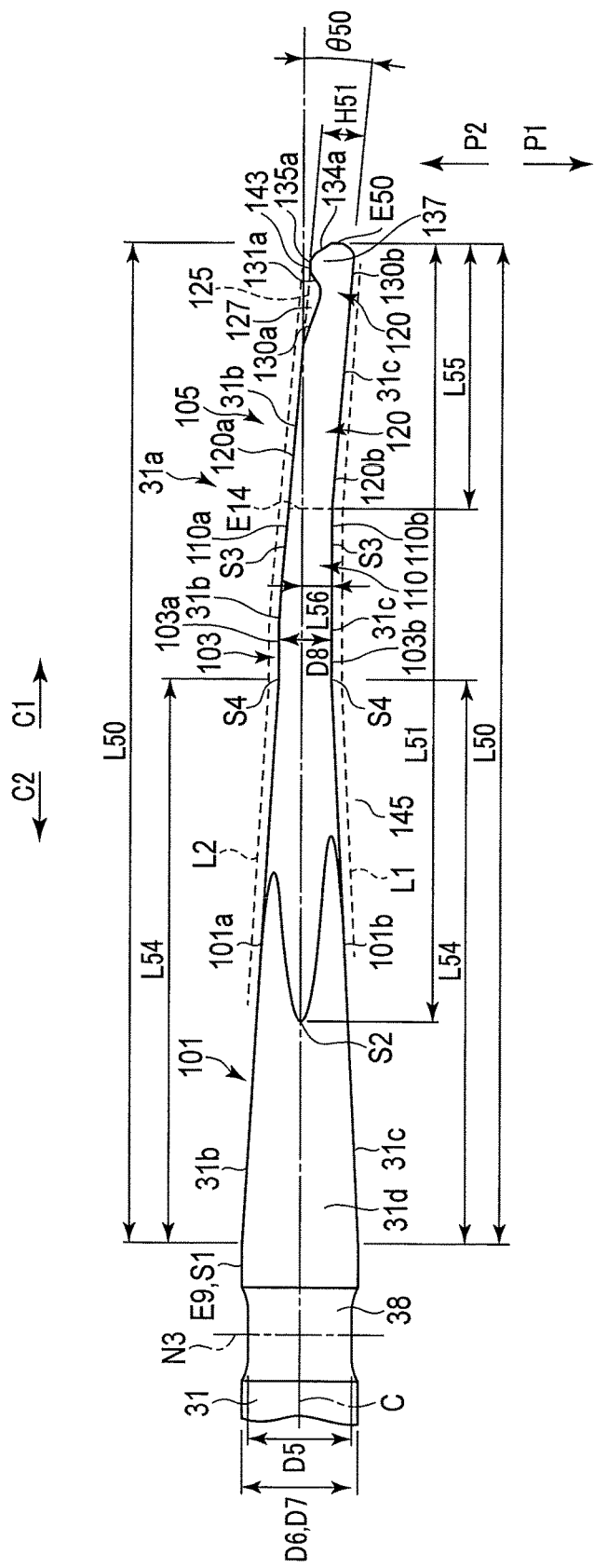
FIG. 9 is a side view of a distal portion of a probe main body section according to a second embodiment.
Figure 10:
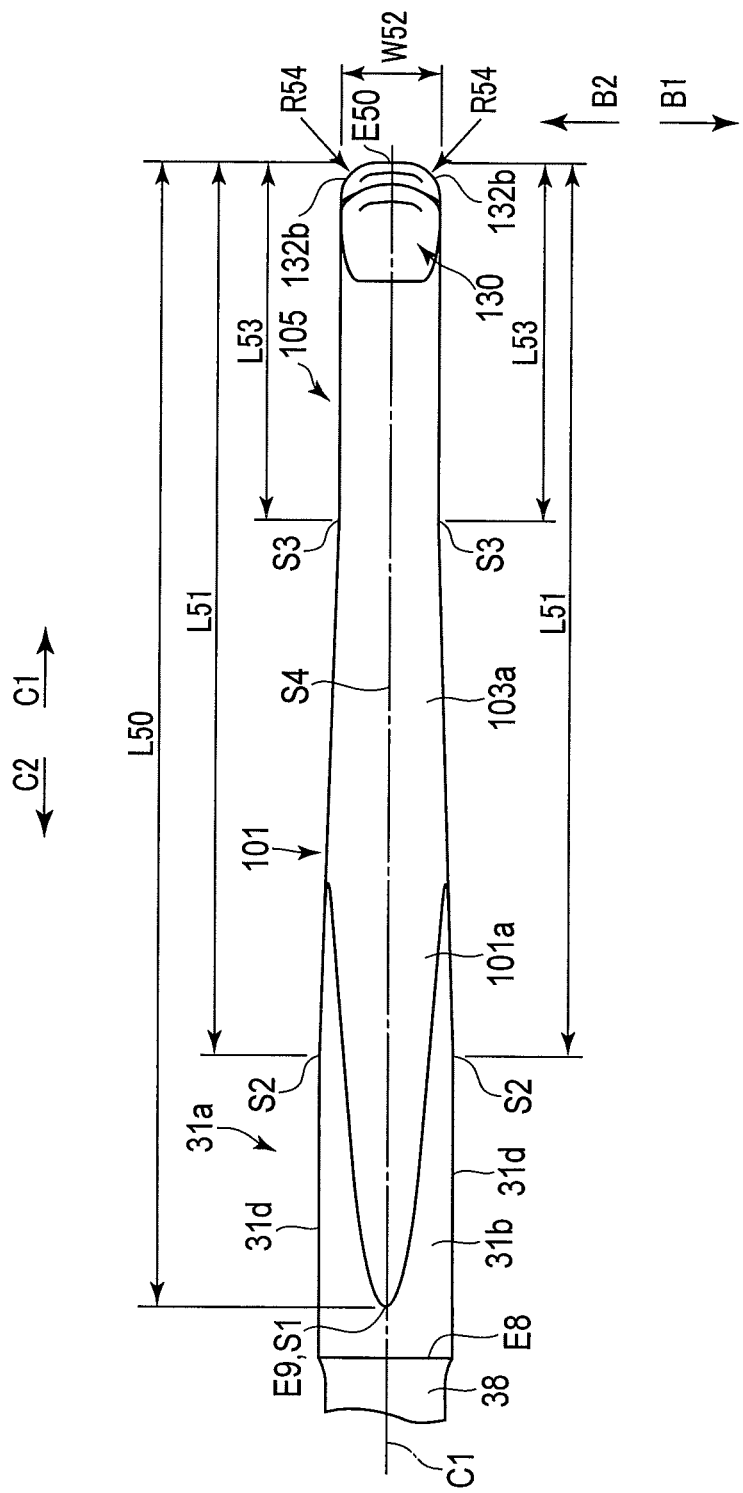
FIG. 10 is a top plan view of the distal portion of the probe main body section according to the second embodiment.

As shown in FIG. 9 and FIG. 11, in a curved surface portion 132a, for example, a corner radius R52 is 0.4 mm. It is preferable that a height H52 of a part 131a relative to a part 130a is 0.7 mm.

As shown in FIG. 11, in the width direction of a curved surface portion 132b, a corner radius. R54 of each curved surface portion 132b is 1 mm.

As shown in FIG. 11, an angle θ56 formed between a part 135a and a perpendicular direction perpendicular to a planar direction of the part 130a is 70 degrees. It is preferable that a longitudinal dimension L60 of the part 135a is 0.2 mm.

As shown in FIG. 11, the curved surface portion 132b is curved smoothly in a circular shape along a longitudinal axis C and toward the rear, and is continuous with a part 134a included in the reference surface 31b. In a height direction of a curved portion 132c between the curved surface portion 132b and the part 134a, a corner radius R55 is 0.4 mm. The part 134a is bent at an angle θ57 relative to the longitudinal axis C. The angle θ57 is 55 degrees.

As shown in FIG. 11, the part 134a is curved smoothly in a circular shape along the longitudinal axis C and toward the rear, and is continuous with the part 135a. In a height direction of a curved portion 132d between the part 134a and the part 135a, a corner radius R56 is 0.4 mm. The part 135a is bent at an angle θ58 relative to the longitudinal axis C. The angle θ58 is 25 degrees.

As shown in FIG. 11, it is preferable that a longitudinal dimension L61 in a longitudinal direction between a distal end E50 formed in the curved surface portion 132b and a blade tip portion 143 is 0.6 mm.

As shown in FIG. 11, the part 135a is bent relative to the blade tip portion 143 in a bending direction of a part 120a about the blade tip portion 143 so that the whole surface of the part 135a including the blade tip portion 143 is disposed on an extension line 125 of the part 120a. Alternatively, the part 135a is bent relative to the blade tip portion 143 in the bending direction of the part 120a about the blade tip portion 143 so that the whole surface of the part 135a including the blade tip portion 143 is positioned on a side opposite to the longitudinal axis C with respect to a boundary that is the extension line 125 of the part 120a. That is, the whole surface of the part 135a including the blade tip portion 143 is disposed on the same plane as the extension line 125 or on a plane below the extension line 125.

As shown in FIG. 11, each of the part 131a and the part 135a including the blade tip portion 143 is formed into a circular shape. In this case, it is preferable that a longitudinal dimension L62 between a central position to form a circle of the blade tip portion 143 and the blade tip portion 143 is 2 mm. The central position is formed on a part 130a side.

In the present embodiment, it is possible to obtain effects similar to those of the first embodiment. In the present embodiment, the blade tip portion 141 is omitted, and the curved portions 132c and 132d can further inhibit generation of cavitation. Each of the part 131a and the part 135a including the blade tip portion 143 is formed into the circular shape. Consequently, treating properties to an affected area 200 can improve.

Although the embodiments, etc. of the present invention have been described above, the present invention is not limited to the above-described embodiments, etc., and, needless to say, various modifications can be made without departing from the spirit of the invention.

What is claimed is:

1. An ultrasonic probe comprising:
   a probe main body section which is extended along a longitudinal axis and to which ultrasonic vibration is transmitted from a proximal side to a distal side;
   a tapered section which is disposed on the distal side with respect to the probe main body section and in which a sectional area perpendicular to the longitudinal axis decreases from the proximal side toward the distal side;
   a curving section which is disposed on the distal side with respect to the tapered section, which is bent relative to the probe main body section and the tapered section in a first intersecting direction in a case where a certain direction intersecting the longitudinal axis is defined as the first intersecting direction and a side opposite to the first intersecting direction is defined as a second intersecting direction, and which extends in a direction of the longitudinal axis,
   the curving section having:
      a lower surface directed on the side of the first intersecting direction and
      an upper surface directed on the side of the second intersecting direction; and
   a treating section which is disposed on the distal side with respect to the curving section, to cut a treatment target, wherein:
   a start position at which the lower surface starts bending relative to the longitudinal axis on the side of the first intersecting direction is positioned more distally than a start position at which the upper surface starts bending relative to the longitudinal axis on the side of the first intersecting direction,
   the entire tapered section, the entire curving section, and the entire treating section are always disposed within a projection plane of the probe main body section, when the probe main body section is viewed along the longitudinal axis from the proximal side toward the distal side,
   a relay extending section in which a sectional area perpendicular to the longitudinal axis is uniform from the proximal side toward the distal side is interposed between the tapered section and the curving section, and
   the upper surface of the curving section includes a first surface which intersects the longitudinal axis of the probe main body section.

2. The ultrasonic probe according to claim 1, wherein from a proximal side of the longitudinal axis toward a distal side thereof,
   a distal portion of the probe main body section is continuous with a proximal portion of the tapered section,
   a distal portion of the tapered section is continuous with a proximal portion of the relay extending section,
   a distal portion of the relay extending section is continuous with a proximal portion of the curving section, and
   a distal portion of the curving section is continuous with a proximal portion of the treating section.

3. The ultrasonic probe according to claim 2, wherein a lower surface of the treating section which is directed on the first intersecting direction side, a lower surface of the relay extending section which is directed on the first intersecting direction side and the lower surface of the curving section form a space as an escaping portion.

4. The ultrasonic probe according to claim 1, wherein a central axis of the curving section is bent at an angle of 5 degrees or more and 20 degrees or less relative to the longitudinal axis of the probe main body section.

5. An ultrasonic treatment instrument comprising:
   the ultrasonic probe according to claim 1; and
   a transducer unit connected to the ultrasonic probe.

6. The ultrasonic probe according to claim 1, wherein the upper surface of the curving section includes a second surface which is continuous with the first surface at a distal side of the longitudinal axis and is bent from the first surface toward the side of the first intersecting direction.

7. The ultrasonic probe according to claim 1, wherein the first surface is parallel to the lower surface.

8. The ultrasonic probe according to claim 1, wherein the curving section includes a sectional area decreasing portion and a sectional area uniform portion.

9. The ultrasonic probe according to claim 8, wherein the treating section includes a blade tip portion configured to treat a knee joint.

10. The ultrasonic probe according to claim 1, wherein respective start positions are positioned on a distal portion side of the curving section with respect to a most distal vibration node when the ultrasonic vibration is transmitted from the proximal side to the distal side in the longitudinal axis of the probe main body section.

11. The ultrasonic probe according to claim 1, wherein the projection plane is aligned along the probe main body section having a greatest cross-sectional diameter.

12. The ultrasonic probe according to claim 1, wherein the projection plane is aligned along a distal end of the probe main body section.

* * * * *